(12) United States Patent
Torrie

(10) Patent No.: US 9,826,992 B2
(45) Date of Patent: Nov. 28, 2017

(54) MULTIPLE PORTAL GUIDE

(75) Inventor: Paul Alexander Torrie, Marblehead, MA (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 12/794,142

(22) Filed: Jun. 4, 2010

(65) Prior Publication Data
US 2010/0241106 A1 Sep. 23, 2010

Related U.S. Application Data

(63) Continuation-in-part of application No. 12/032,168, filed on Feb. 15, 2008, now Pat. No. 8,956,278.

(60) Provisional application No. 61/015,811, filed on Dec. 21, 2007, provisional application No. 61/187,797, filed on Jun. 17, 2009.

(51) Int. Cl.
| | |
|---|---|
| *A61B 1/04* | (2006.01) |
| *A61B 17/17* | (2006.01) |
| *A61B 17/00* | (2006.01) |
| *A61B 17/34* | (2006.01) |

(Continued)

(52) U.S. Cl.
CPC ........ *A61B 17/175* (2013.01); *A61B 17/1714* (2013.01); *A61B 17/1739* (2013.01); *A61B 90/11* (2016.02); *A61B 2017/00477* (2013.01); *A61B 2017/3405* (2013.01); *A61B 2017/3407* (2013.01); *A61B 2017/3411* (2013.01); *A61B 2090/0811* (2016.02); *A61B 2090/3937* (2016.02); *A61B 2090/3966* (2016.02)

(58) Field of Classification Search
CPC .............. A61B 17/175; A61B 17/1714; A61B 17/1739; A61B 2017/00477; A61B 2017/3405; A61B 2017/3407
USPC .................................... 600/102, 114; 606/96
See application file for complete search history.

(56) References Cited

U.S. PATENT DOCUMENTS

| | | | |
|---|---|---|---|
| 86,016 A | 1/1869 | Howell | |
| 3,299,883 A | 1/1967 | Rubens | |

(Continued)

FOREIGN PATENT DOCUMENTS

| | | |
|---|---|---|
| CN | 1069644 A | 3/1993 |
| CN | 1625370 A | 6/2005 |

(Continued)

OTHER PUBLICATIONS

Victor M. Ilizaliturri, Jr., M.D., et al, "An Aiming Guide for Anterior Portal Placement in Hip Arthroscopy", Arthroscopy: The Journal of Arthroscopic and Related Surgery, vol. 19, No. 9 Nov. 2003: E77.

(Continued)

*Primary Examiner* — Timothy J Neal
(74) *Attorney, Agent, or Firm* — Burns & Levinson LLP; Joseph M. Maraia

(57) ABSTRACT

The present disclosure relates to a guide assembly. The guide assembly includes a guide having a body having a first set of marks and a joint including at least one through hole, the joint configured for sliding along the length of the body; and a first surgical device having a second set of marks, wherein the guide is coupled to the first surgical device and a longitudinal axis of the through hole is co-radial with a mark of the second set of marks when the joint is located at a mark of the first set of marks. Other guides are also disclosed.

14 Claims, 19 Drawing Sheets

(51) Int. Cl.
*A61B 90/11* (2016.01)
*A61B 90/00* (2016.01)

(56) References Cited

U.S. PATENT DOCUMENTS

| | | | |
|---|---|---|---|
| 3,347,234 A | 10/1967 | Voss | |
| 3,508,334 A | 4/1970 | Weissman | |
| 3,604,487 A | 9/1971 | Gilbert | |
| 3,867,932 A | 2/1975 | Huene | |
| 4,039,266 A | 8/1977 | O'Connell | |
| 4,159,716 A | 7/1979 | Borchers | |
| 4,254,762 A | 3/1981 | Yoon | |
| 4,363,250 A | 12/1982 | Suga | |
| 4,580,563 A | 4/1986 | Gross | |
| 4,708,139 A | 11/1987 | Dunbar | |
| 4,712,547 A | 12/1987 | Bonnet | |
| 4,721,116 A | 1/1988 | Schintgen | |
| 4,722,331 A | 2/1988 | Fox | |
| 4,739,751 A | 4/1988 | Sapega et al. | |
| 4,830,023 A | 5/1989 | de Toledo et al. | |
| 4,896,663 A | 1/1990 | Vandewalls | |
| 4,899,756 A | 2/1990 | Sonek | |
| 4,917,699 A | 4/1990 | Chervitz | |
| 4,960,134 A | 10/1990 | Webster | |
| 5,112,337 A | 5/1992 | Paulos et al. | |
| 5,152,764 A | 10/1992 | Goble | |
| 5,152,790 A | 10/1992 | Rosenberg et al. | |
| 5,163,940 A * | 11/1992 | Bourque | A61B 17/1764 606/103 |
| 5,176,515 A | 1/1993 | Andrews | |
| 5,197,971 A | 3/1993 | Bonutti | |
| 5,207,753 A | 5/1993 | Badrinath | |
| 5,231,989 A | 8/1993 | Middleman et al. | |
| 5,250,055 A | 10/1993 | Moore et al. | |
| RE34,502 E | 1/1994 | Webster, Jr. | |
| 5,289,963 A | 3/1994 | McGarry et al. | |
| 5,292,330 A | 3/1994 | Shutt | |
| 5,320,626 A | 6/1994 | Schmieding | |
| 5,330,468 A | 7/1994 | Burkhart | |
| 5,345,937 A | 9/1994 | Middleman et al. | |
| 5,356,064 A | 10/1994 | Green et al. | |
| 5,364,002 A | 11/1994 | Green et al. | |
| 5,366,479 A | 11/1994 | McGarry et al. | |
| 5,409,490 A | 4/1995 | Ethridge | |
| 5,458,602 A | 10/1995 | Goble et al. | |
| 5,484,095 A | 1/1996 | Green et al. | |
| 5,497,933 A | 3/1996 | DeFonzo et al. | |
| 5,514,144 A | 5/1996 | Bolton | |
| 5,520,693 A | 5/1996 | McGuire et al. | |
| 5,545,175 A | 8/1996 | Abidin et al. | |
| 5,549,617 A | 8/1996 | Green | |
| 5,562,664 A * | 10/1996 | Durlacher et al. | 606/96 |
| 5,562,689 A | 10/1996 | Green et al. | |
| 5,573,538 A | 11/1996 | Laboureau | |
| 5,575,801 A | 11/1996 | Habermeyer et al. | |
| 5,584,839 A | 12/1996 | Gieringer | |
| 5,601,550 A | 2/1997 | Esser | |
| 5,609,596 A | 3/1997 | Pepper | |
| 5,613,971 A * | 3/1997 | Lower et al. | 606/96 |
| 5,637,112 A | 6/1997 | Moore et al. | |
| 5,643,273 A | 7/1997 | Clark | |
| 5,643,294 A | 7/1997 | Tovey et al. | |
| 5,645,549 A | 7/1997 | Boyd et al. | |
| 5,665,072 A | 9/1997 | Yoon | |
| 5,667,509 A | 9/1997 | Westin | |
| 5,667,513 A | 9/1997 | Torrie et al. | |
| 5,681,320 A | 10/1997 | McGuire | |
| 5,688,284 A * | 11/1997 | Chervitz et al. | 606/96 |
| 5,716,360 A | 2/1998 | Baldwin et al. | |
| 5,720,753 A | 2/1998 | Sander et al. | |
| 5,776,075 A | 7/1998 | Palmer | |
| 5,817,109 A | 10/1998 | McGarry et al. | |
| 5,820,630 A | 10/1998 | Lind | |
| 5,829,444 A | 11/1998 | Ferree et al. | |
| 5,843,108 A | 12/1998 | Samuels | |
| 5,865,361 A | 2/1999 | Milliman et al. | |
| 5,885,300 A | 3/1999 | Tokuhashi et al. | |
| 5,891,150 A | 4/1999 | Chan | |
| 5,968,050 A * | 10/1999 | Torrie | 606/87 |
| 6,004,332 A | 12/1999 | Yoon et al. | |
| 6,019,767 A | 2/2000 | Howell | |
| 6,022,356 A | 2/2000 | Noyes et al. | |
| 6,024,708 A | 2/2000 | Bales et al. | |
| 6,048,354 A | 4/2000 | Lawrence | |
| 6,079,606 A | 6/2000 | Milliman et al. | |
| 6,120,511 A * | 9/2000 | Chan | 606/96 |
| 6,123,678 A | 9/2000 | Palmer | |
| 6,129,683 A | 10/2000 | Sutton | |
| 6,132,368 A | 10/2000 | Cooper | |
| 6,136,010 A | 10/2000 | Modesitt et al. | |
| 6,187,011 B1 | 2/2001 | Torrie | |
| 6,200,322 B1 | 3/2001 | Branch et al. | |
| 6,210,415 B1 | 4/2001 | Bester | |
| 6,216,029 B1 | 4/2001 | Paltieli | |
| 6,241,139 B1 | 6/2001 | Milliman et al. | |
| 6,254,605 B1 | 7/2001 | Howell | |
| 6,254,606 B1 | 7/2001 | Carney et al. | |
| 6,267,763 B1 | 7/2001 | Castro | |
| 6,330,965 B1 | 12/2001 | Milliman et al. | |
| 6,342,057 B1 | 1/2002 | Brace et al. | |
| 6,375,658 B1 | 4/2002 | Hangody et al. | |
| 6,450,948 B1 | 9/2002 | Matsuura et al. | |
| 6,490,467 B1 | 12/2002 | Bucholz et al. | |
| 6,491,645 B1 | 12/2002 | Gaber | |
| 6,508,496 B1 | 1/2003 | Huang | |
| 6,582,451 B1 | 6/2003 | Marucci | |
| 6,656,205 B1 | 12/2003 | Manhes | |
| 6,669,073 B2 | 12/2003 | Milliman et al. | |
| 6,701,812 B1 | 3/2004 | Sawamura | |
| 6,716,228 B2 | 4/2004 | Tal | |
| 6,840,932 B2 | 1/2005 | Lang | |
| 6,918,916 B2 | 7/2005 | Gobel et al. | |
| 6,929,647 B2 | 8/2005 | Cohen | |
| 6,953,139 B2 | 10/2005 | Milliman et al. | |
| 6,958,067 B2 * | 10/2005 | Whittaker et al. | 606/98 |
| 6,964,668 B2 | 11/2005 | Modesitt et al. | |
| 7,001,400 B1 | 2/2006 | Modesitt et al. | |
| 7,090,680 B2 | 8/2006 | Bonati et al. | |
| 7,112,208 B2 | 9/2006 | Morris et al. | |
| 7,192,431 B2 | 3/2007 | Hangody et al. | |
| 7,201,756 B2 | 4/2007 | Ross et al. | |
| 7,204,839 B2 | 4/2007 | Dreyfuss et al. | |
| 7,235,087 B2 | 6/2007 | Modesitt et al. | |
| 7,264,622 B2 | 9/2007 | Michelson | |
| 7,303,107 B2 | 12/2007 | Milliman et al. | |
| 7,341,564 B2 | 3/2008 | Zwiefel | |
| 7,341,596 B2 | 3/2008 | Heppler | |
| 7,351,201 B2 | 4/2008 | Ouchi | |
| 7,422,594 B2 | 9/2008 | Zander | |
| 7,481,824 B2 | 1/2009 | Boudreaux et al. | |
| 7,488,327 B2 | 2/2009 | Rathbun et al. | |
| 7,565,993 B2 | 7/2009 | Milliman et al. | |
| 7,594,917 B2 | 9/2009 | Whittaker et al. | |
| 7,624,902 B2 | 12/2009 | Marczyk et al. | |
| 7,624,903 B2 | 12/2009 | Green et al. | |
| 7,625,378 B2 | 12/2009 | Foley | |
| 7,681,772 B2 | 3/2010 | Green et al. | |
| 7,828,187 B2 | 11/2010 | Green et al. | |
| 7,842,042 B2 | 11/2010 | Reay-Young | |
| 7,871,422 B2 | 1/2011 | Shibata | |
| 7,985,239 B2 | 7/2011 | Suzuki | |
| 8,197,482 B2 | 6/2012 | Stone | |
| 8,282,647 B2 | 10/2012 | Re | |
| 8,317,862 B2 | 11/2012 | Troger et al. | |
| 8,343,161 B2 | 1/2013 | Re | |
| 8,523,872 B2 | 9/2013 | Ek | |
| 8,617,168 B2 | 12/2013 | Bourque et al. | |
| 8,685,033 B2 | 4/2014 | Johnson et al. | |
| 8,690,885 B2 | 4/2014 | Smith | |
| 8,771,273 B2 | 7/2014 | Homan et al. | |
| 8,790,352 B2 | 7/2014 | Smith et al. | |
| 8,840,615 B2 | 9/2014 | Bourque | |
| 2001/0012967 A1 * | 8/2001 | Mosseri | A61B 17/1666 623/23.12 |

(56) References Cited

U.S. PATENT DOCUMENTS

| | | |
|---|---|---|
| 2001/0016746 A1 | 8/2001 | McGuire et al. |
| 2001/0053934 A1 | 12/2001 | Schmieding |
| 2002/0019649 A1 | 2/2002 | Sikora et al. |
| 2002/0117533 A1 | 8/2002 | Milliman et al. |
| 2002/0117534 A1 | 8/2002 | Green et al. |
| 2002/0133165 A1 | 9/2002 | Whittaker et al. |
| 2002/0143341 A1 | 10/2002 | Biedermann et al. |
| 2002/0143342 A1 | 10/2002 | Hangody et al. |
| 2002/0143354 A1 | 10/2002 | Lang |
| 2002/0156376 A1 | 10/2002 | Wang et al. |
| 2002/0173849 A1 | 11/2002 | Mckernan et al. |
| 2003/0009173 A1 | 1/2003 | McGuire et al. |
| 2003/0009218 A1 | 1/2003 | Boucher et al. |
| 2003/0083688 A1 | 5/2003 | Simonson |
| 2003/0083695 A1 | 5/2003 | Morris |
| 2003/0093093 A1 | 5/2003 | Modesitti et al. |
| 2003/0208206 A1 | 11/2003 | Gitis et al. |
| 2003/0216742 A1 | 11/2003 | Wetzler et al. |
| 2004/0015170 A1 | 1/2004 | Tallarida et al. |
| 2004/0049195 A1 | 3/2004 | Singhatat et al. |
| 2004/0073227 A1 | 4/2004 | Dreyfuss et al. |
| 2004/0147932 A1 | 7/2004 | Burkinshaw et al. |
| 2004/0181246 A1 | 9/2004 | Heppler |
| 2004/0193172 A1 | 9/2004 | Ross et al. |
| 2004/0220588 A1 | 11/2004 | Kermode et al. |
| 2004/0267276 A1 | 12/2004 | Camino et al. |
| 2005/0027299 A1 | 2/2005 | Metzger |
| 2005/0033365 A1 | 2/2005 | Courage |
| 2005/0113841 A1 | 5/2005 | Sheldon |
| 2005/0149045 A1 | 7/2005 | Elliott |
| 2005/0165420 A1 | 7/2005 | Cha |
| 2005/0177171 A1* | 8/2005 | Wetzler ............... A61B 17/17 606/96 |
| 2005/0177179 A1 | 8/2005 | Baynham et al. |
| 2005/0222601 A1 | 10/2005 | Erhard |
| 2005/0228399 A1 | 10/2005 | Kubo et al. |
| 2005/0245924 A1 | 11/2005 | Tuke et al. |
| 2005/0245934 A1 | 11/2005 | Tuke |
| 2005/0261692 A1 | 11/2005 | Carrison et al. |
| 2006/0041263 A1 | 2/2006 | Chu et al. |
| 2006/0069394 A1 | 3/2006 | Weiler et al. |
| 2006/0085006 A1 | 4/2006 | Ek et al. |
| 2006/0106398 A1 | 5/2006 | Lauryssen et al. |
| 2006/0119014 A1 | 6/2006 | Towers et al. |
| 2006/0155290 A1 | 7/2006 | Shino |
| 2006/0195106 A1 | 8/2006 | Jones et al. |
| 2006/0195112 A1* | 8/2006 | Ek .................................. 606/86 |
| 2006/0271059 A1* | 11/2006 | Reay-Young ......... A61F 2/0805 606/96 |
| 2007/0118136 A1 | 5/2007 | Ek |
| 2007/0152014 A1 | 7/2007 | Gillujm et al. |
| 2007/0179340 A1 | 8/2007 | Jorgenson |
| 2007/0191852 A1 | 8/2007 | Shimko et al. |
| 2007/0191853 A1 | 8/2007 | Stone |
| 2007/0233128 A1 | 10/2007 | Schmieding et al. |
| 2007/0233136 A1 | 10/2007 | Wozencroft |
| 2007/0233151 A1 | 10/2007 | Chudik |
| 2007/0233241 A1 | 10/2007 | Graf et al. |
| 2007/0244508 A1 | 10/2007 | Weizman |
| 2007/0270804 A1 | 11/2007 | Chudik |
| 2007/0276370 A1 | 11/2007 | Altarac et al. |
| 2007/0282356 A1 | 12/2007 | Remiszewski et al. |
| 2007/0282358 A1 | 12/2007 | Remiszewski et al. |
| 2008/0027435 A1 | 1/2008 | Zucherman et al. |
| 2008/0027457 A1 | 1/2008 | Dienst et al. |
| 2008/0097453 A1 | 4/2008 | Stone |
| 2008/0103506 A1 | 5/2008 | Volpi et al. |
| 2008/0140748 A1 | 6/2008 | Lada |
| 2008/0188859 A1 | 8/2008 | Reitzig et al. |
| 2008/0221581 A1 | 9/2008 | Shoham |
| 2008/0306485 A1 | 12/2008 | Coon et al. |
| 2008/0306487 A1 | 12/2008 | Hart |
| 2009/0018654 A1 | 1/2009 | Schmieding et al. |
| 2009/0048673 A1 | 2/2009 | Le Huec |
| 2009/0069845 A1 | 3/2009 | Frushell et al. |
| 2009/0076512 A1 | 3/2009 | Ammann et al. |
| 2009/0143784 A1 | 6/2009 | Petersen et al. |
| 2009/0157081 A1 | 6/2009 | Homan et al. |
| 2009/0157110 A1 | 6/2009 | Muto et al. |
| 2009/0163766 A1 | 6/2009 | Torrie |
| 2009/0163935 A1 | 6/2009 | McCarthy et al. |
| 2009/0171355 A1 | 7/2009 | Amis et al. |
| 2009/0171360 A1 | 7/2009 | Whelan |
| 2009/0216236 A1 | 8/2009 | Re |
| 2009/0216243 A1 | 8/2009 | Re |
| 2009/0222013 A1 | 9/2009 | Graf et al. |
| 2009/0228031 A1 | 9/2009 | Ritter et al. |
| 2009/0254093 A1 | 10/2009 | White |
| 2009/0281545 A1 | 11/2009 | Stubbs |
| 2009/0306675 A1 | 12/2009 | Wong et al. |
| 2010/0016984 A1 | 1/2010 | Trabish |
| 2010/0030029 A1 | 2/2010 | Markham |
| 2010/0030116 A1 | 2/2010 | Chana |
| 2010/0042106 A1 | 2/2010 | Bryant |
| 2010/0049200 A1 | 2/2010 | Re |
| 2010/0049201 A1 | 2/2010 | Re |
| 2010/0057077 A1 | 3/2010 | Ducharme |
| 2010/0068233 A1 | 3/2010 | Bangera et al. |
| 2010/0121337 A1 | 5/2010 | Pandya |
| 2010/0137872 A1 | 6/2010 | Kam et al. |
| 2010/0137924 A1 | 6/2010 | Tuke |
| 2010/0241106 A1 | 9/2010 | Torrie |
| 2010/0249930 A1 | 9/2010 | Myers |
| 2010/0256645 A1 | 10/2010 | Zajac et al. |
| 2010/0268241 A1 | 10/2010 | Flom et al. |
| 2010/0292743 A1 | 11/2010 | Singhal |
| 2011/0087258 A1 | 4/2011 | Sluss |
| 2011/0251621 A1 | 10/2011 | Sluss |
| 2011/0282350 A1 | 11/2011 | Kowarsch et al. |
| 2011/0313478 A1 | 12/2011 | Herdrich et al. |
| 2012/0046526 A1 | 2/2012 | Boettner et al. |
| 2012/0059382 A1 | 3/2012 | Paulos |
| 2012/0059469 A1 | 3/2012 | Myers et al. |
| 2012/0109136 A1 | 5/2012 | Bourque et al. |
| 2012/0116402 A1 | 5/2012 | Schneider |
| 2012/0150301 A1 | 6/2012 | Gamache et al. |
| 2012/0197261 A1 | 8/2012 | Rocci et al. |
| 2013/0085494 A1 | 4/2013 | Weisenburgh et al. |
| 2014/0107657 A1 | 4/2014 | Norton et al. |
| 2014/0303635 A1 | 10/2014 | Smith et al. |

FOREIGN PATENT DOCUMENTS

| | | |
|---|---|---|
| CN | 201182625 Y | 1/2009 |
| CN | 201612662 U | 10/2010 |
| DE | 102007057075 A1 | 5/2009 |
| EP | 0643945 A2 | 3/1995 |
| EP | 1444959 A1 | 8/2004 |
| EP | 1649818 A2 | 4/2006 |
| EP | 1882456 A | 1/2008 |
| EP | 1882456 A2 | 1/2008 |
| EP | 1917921 A2 | 5/2008 |
| EP | 2311394 A1 | 4/2011 |
| FR | 2716364 A | 8/1995 |
| FR | 2716364 A1 | 8/1995 |
| FR | 2901465 A1 | 11/2007 |
| FR | 2906452 A1 | 4/2008 |
| FR | 2911264 A1 | 7/2008 |
| FR | 2918554 A1 | 1/2009 |
| GB | 2230453 A | 10/1990 |
| JP | H10-174689 | 6/1998 |
| JP | 2002102236 A | 4/2002 |
| JP | 2003-531676 | 10/2003 |
| JP | 2003531676 | 10/2003 |
| JP | 2005507697 A | 3/2005 |
| JP | 2009195705 A | 9/2009 |
| JP | 2009261812 | 11/2009 |
| JP | 2010527705 | 8/2010 |
| JP | 2011507639 A | 3/2011 |
| JP | 2011520475 A | 7/2011 |
| JP | 2012075604 A | 4/2012 |
| RU | 2125844 C1 | 2/1999 |
| RU | 2241394 C2 | 12/2004 |
| RU | 46642 U1 | 7/2005 |

(56) References Cited

FOREIGN PATENT DOCUMENTS

| WO | 8800458 A1 | 1/1988 |
| WO | 9929237 A1 | 6/1999 |
| WO | 9956628 | 11/1999 |
| WO | 0140748 A1 | 6/2001 |
| WO | 0182838 A2 | 11/2001 |
| WO | WO0182838 A2 | 11/2001 |
| WO | 0236020 A1 | 5/2002 |
| WO | 2003037163 A2 | 5/2003 |
| WO | 2005037065 A2 | 4/2005 |
| WO | 2005037150 A1 | 4/2005 |
| WO | 2006088452 A2 | 8/2006 |
| WO | WO2006074321 A3 | 1/2007 |
| WO | 2009082497 A1 | 7/2009 |
| WO | WO2011153094 A1 | 12/2011 |
| WO | 2012103535 A1 | 8/2012 |
| WO | 2014107729 A2 | 7/2014 |

OTHER PUBLICATIONS

Michael Dienst, M.D., et al, "Safe Arthroscopic Access to the Central Compartment of the Hip", Arthroscopy: The Journal of Arthoscopic and Related Surgery, vol. 21, No. 12 Dec. 2005: pp. 1510-1514.
J.W. Thomas Byrd, M.D., et al, Hip Arthroscopy: An Anatomic Study of Portal Placement and Relationship to the Extra-Articular Structures, Arthroscopy: The Journal of Arthroscopic and Related Surgery, vol. 11, No. 4 Aug. 1995: pp. 418-423.
Victor M. Illizaliturri, Jr., M.D., "Hip Arthroscopy Using the Smith & Nephew Hip Access System", Smith & Nephew Hip Series Technique Guide.
J.W. Thomas Byrd, M.D., "Hip Arthroscopy Principles and Application", Smith & Nephew Hip Series Technique Guide.
Office Action for U.S. Appl. No. 12/032,168, mailed Aug. 15, 2011.
Final Office Action for U.S. Appl. No. 12/032,168, mailed Jan. 9, 2012.
International Preliminary Report on Patentability for International Application No. PCT/US2011/038351, mailed Dec. 4, 2012.
Office Action for U.S. Appl. No. 12/794,142, mailed Jan. 16, 2013.
International Search Report and Written Opinion for International Patent Application PCT/US2011/038351 mailed Oct. 24, 2011.
Michael Dienst, MD., et al, "Safe Arthroscopic Access to the Central Compartment of the Hip", Arthroscopy: The Journal of Arthoscopic and Related Surgery, vol. 21, No. 12 Dec. 2005: pp. 1510-1514.
JW. Thomas Byrd, MD., et al, Hip Arthroscopy: An Anatomic Study of Portal Placement and Relationship to the Extra-Articular Structures, Arthroscopy: The Journal of Arthroscopic and Related Surgery, vol. 11, No. 4 Aug. 1995: pp. 418-423.
Victor M. Illizaliturri. Jr., MD., "Hip Arthroscopy Using the Smith & Nephew Hip Access System", Smith & Nephew Hip Series Technique Guide © 2004.
JW. Thomas Byrd, MD., "Hip Arthroscopy Principles and Application", Smith & Nephew Hip Series Technique Guide © 2001.
Office Action for U.S. Appl. No. 12/794,142,mailed Aug. 3, 2012.
International Search Report and Written Opinion for International Application No. PCT/US2012/028537, mailed May 25, 2012.
Notice of Reasons for Rejection for Japanese Application No. 2010-539524, mailed Oct. 9, 2012.
International Preliminary Report on Patentability for International Application No. PCT/US2011/1038351, mailed Dec. 4, 2012.
Thomas G. Sampson, MD., "Arthroscopic Treatment of Femoracetabular Impingement," Smith & Nephew Hip Series Technique Guide © 2006.
Office Action for U.S. Appl. No. 12/032,168, mailed Jan. 9, 2012.
Victor M. Ilizaliturri, Jr., MD., et al, "An Aiming Guide for Anterior Portal Placement in Hip Arthroscopy", Arthroscopy: The Journal of Arthroscopic and Related Surgery, vol. 19, No. 9 Nov. 2003: E77.
Second Office Action for Japanese Patent Application No. 2010-539524, mailing date Apr. 16, 2013.
Third Office Action for Japanese Patent Application No. 2010-539524, mailing date Nov. 26, 2013.
Patent Examination Report No. 1 for Australian Patent Application No. 2008341062, mailed Mar. 20, 2013.
Decision for Rejection for Japanese Patent Application No. 2010-539524, mailing date Jun. 2, 2014.
Communication of Substantive Examination Report for related Mexican Application No. MX/a/2013/010271 mailed Nov. 12, 2015.
Second Office Action for Chinese Application No. 201180038188.3 dated May 21, 2015.
Patent Examination Report No. 1 from related Australian Application No. 2011261677 issued May 4, 2015.
Substantive Examination from related Russian Application No. 201257126/14(090134).
First Office Action from related Chinese Application No. 201280012304 issued Jul. 13, 2015.
Decision of Rejection from related Japanese Application No. 2013-513252 mailed Sep. 14, 2015.
Communication pursuant to Article 94(3) EPC for related European Application No. 12712462.6 dated Feb. 3, 2015.
First Office Action for Chinese application 201180038188.3, mailing date Sep. 28, 2014.
Patent Examination Report No. 1 from related Austrailian Application No. 2012225353 issued Jul. 30, 2015.
Communication of the Substantive Examination Report for related Mexican Application No. MX/a/2013/010271 mailed Jun. 16, 2015.
Patent Examination Report No. 2 in related Australian Application No. 2011261677 issued Jan. 20, 2016.
Substantive Examination Report from related Mexican Application No. MX/a/2013/010271 mailed Jan. 18, 2016.
Communication pursuant to Article 94(3) EPC issued in European Application No. 12712462.6 dated Feb. 22, 2016.
Patent Examination Report No. 2 for related Australian Patent Application No. 2012225323 issued Feb. 17, 2016.
Patent Examination Report No. 3 for related Australian Patent Application No. 2012225323 issued Mar. 8, 2016.
Office Action from related Russian Application No. 2013144962/14(069528) issued Feb. 3, 2016.
Second Office Action from related Chinese Application No. 201280012304.9 issued Apr. 19, 2016.
Decision of Rejection from related Japanese Application No. 2013-557915 issued Jun. 6, 2016.
Patent Examination Report from related Australian Application No. 2015201256 issued Jun. 22, 2016.
Substantive Examination Report from related Mexican Application No. MX/a/2013/010271 dated Jul. 14, 2016.
Communication from related European Application No. 11727002.5-1664 dated Feb. 6, 2017.
Shino, Konsei, "Triple Bundle ACL Reconstruction Using the Smith and Nephew ENDOBUTTON CL Fixation System" Knee Series. Technique Guide. Andover, Massachusetts: 2007.
Kayvani, K., "Analysis and Esign of Cable Supported Roof Structures," <https://books.google.com/books?id=xIgyl_U1ITkC&pg=PA59&dq=high+tensile+strangth+steel+characteristics+flexibility&source=bl&ots=I2WZYv2_LR&sig=wdmKuugAPuSRTQjyvuqJ7AKqutl&hl=en&sa=X&ei=Ke0eVYS4G8z3sAWPvYC4CA&ved=0CE4Q6AEwBw#v=one_page&q&f=true> accessed May 14, 2015.
Matsuda, D.K., "FAI: An emerging problem in orthopedics," Orthopedics Today, Jul. 2009, Retrieved from www.healio.com on Jan. 11, 2013.
Office Action from related Mexican Application No. MX/a/2013/003496 dated Jun. 6, 2017.
Communication from related EP Application No. 08729966.5-1659 dated Jul. 7, 2017.
Notice of Reasons for Rejection from related Japanese Application No. 2016-12398 dated Jul. 14, 2017.

* cited by examiner

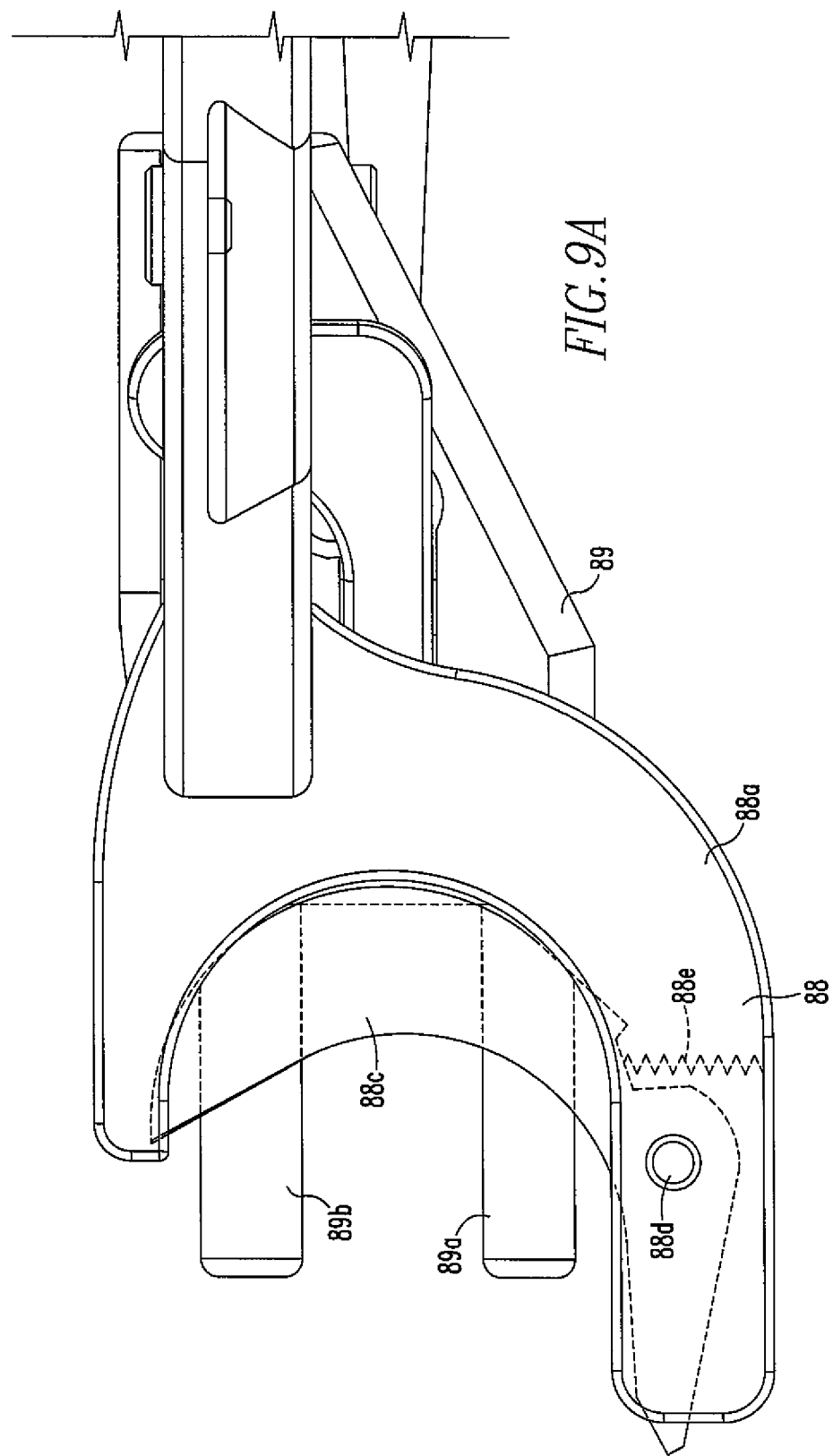

MULTIPLE PORTAL GUIDE

CROSS-REFERENCE TO RELATED APPLICATIONS

This application is a continuation-in-part patent application of U.S. patent application Ser. No. 12/032,168, filed Feb. 15, 2008, which claims the benefit of U.S. patent application Ser. No. 61/015,811, filed Dec. 21, 2007. This application also claims priority to U.S. patent application Ser. No. 61/187,797, filed Jun. 17, 2009. The disclosures of each of these prior filed applications are incorporated herein by reference in their entireties.

BACKGROUND

Field of Technology

The present disclosure relates to medical devices for use in surgery and, more specifically, a guide for use in creating multiple portals during surgery.

Related Art

During arthroscopic surgery, the joint areas of the body, such as the hip, knee, shoulder, and other joint areas, are approached via the use of an endoscope. Some joints are harder to access than others. For example, the hip joint differs from other joints in that a much thicker layer of soft tissue, known as the hip capsule, surrounds it. This thick layer makes changing the trajectory of instruments placed into the joint difficult and the importance of placing portals, or tissue passages, more critical than other joints.

Presently, fluoroscopy is used to place the portals that house the endoscope and the other instruments used during surgery. Multiple x-rays are taken while the surgeon tries various approaches to the joint using a thin needle that may be reinserted several times until the ideal portal placement is found. This process exposes the surgical team to radiation, is time consuming, and can lead to trauma, particularly to the delicate articular cartilage and, in the case of the hip joint, the acetabular labrum.

There is a need for an apparatus and method that would allow for the creation of multiple portals while substantially reducing the possible harmful effects and the amount of time that is required of the present methods.

SUMMARY

In one aspect, the present disclosure relates to a guide assembly. The assembly includes a guide including a body having a first set of marks and a joint including at least one through hole, the joint configured for sliding along the length of the body, and a first surgical device having a second set of marks. The guide is coupled to the first surgical device and a longitudinal axis of the through hole is co-radial with a mark of the second set of marks when the joint is located at a mark of the first set of marks.

In another aspect, the present disclosure relates to a guide assembly. The guide assembly includes a guide including a body having at least one through hole and a first surgical device including an end having a mark. The guide is coupled to the first surgical device and a longitudinal axis of the through hole is co-radial with the mark on the end of the first surgical device.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 9A shows a top view of the lever arm, of the fourth guide assembly, in a first position.

DETAILED DESCRIPTION OF THE EMBODIMENTS

The following description of the preferred embodiment(s) is merely exemplary in nature and is in no way intended to limit the disclosure, its application, or uses.

Figure 1:
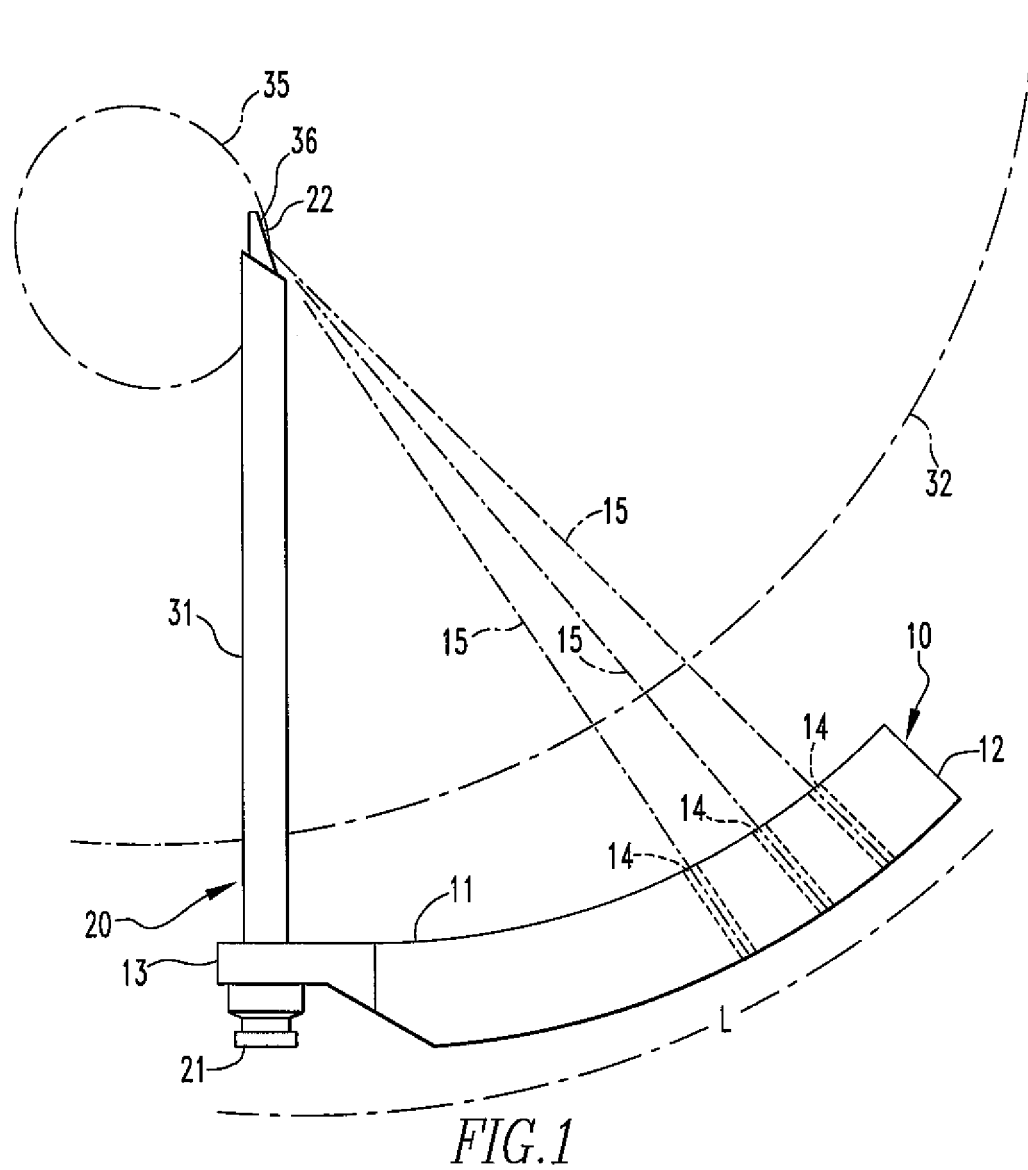
FIGS. 1-4 show front views of a first guide assembly of the present disclosure.

FIG. 1 shows a guide 10 that includes a body 11 having a first end 12, a second end 13, an arc along a length L of the body 11, and at least one through hole 14. Also shown in FIG. 1 is a first surgical instrument 20, such as an endoscope, that includes a first end 21 and a second end 22. The second end 13 of the guide 10 is coupled to the first end 21 of the endoscope 20, via a cannula 40, as further described below, and a longitudinal axis 15 of the through hole 14 intersects, or is co-radial with, the second end 22 of the endoscope 20. As also shown in FIG. 1, the body 11 may include multiple through holes 14, each of which includes a longitudinal axis 15 that intersects, or is co-radial with, the second end 22 of the endoscope 20.

During arthroscopic surgery, especially hip arthroscopy, a first portal 31 is created in a relatively safe position, within a patient's body 32, where damage to internal structures is minimized. The portal 31 may be created via the use of fluoroscopy, as described above, or another method known to one of ordinary skill in the art. The first cannula 40 and endoscope 20 are then inserted through the portal 31, so that a clear view of the inside of the patient's body 32, especially the area 35 where surgery is to be performed (i.e. the hip joint and the capsule surrounding the joint), can be seen by the surgeon. This view also shows the surgeon the anatomy that must be avoided and where a safe area for placing other portals is. As will be further discussed below, the endoscope 20 is disposed within the first cannula 40 such that the second end 22 of the endoscope 20 protrudes through a second end 42 of the cannula 40. After positioning the second end 22 of the endoscope 20 at an area 36 where the surgeon wishes a second portal (FIG. 4, 33) to be placed, such as the inner surface of the hip capsule, the guide 10 is coupled to the first end 21 of the endoscope 20, via the cannula, and the second portal (FIG. 4, 33) is placed relative to the second end 22 of the endoscope 20 by inserting a second surgical device (FIG. 4, 34), such as a second cannula, through one of the through holes 14 and into the patient's body 32. Since the longitudinal axis 15 of the through hole 14 intersects, or is co-radial with, the second end 22 of the endoscope 20, the second cannula 34 would also be co-radial with the second end 22 of the endoscope 20. Furthermore, and as will be described below, this co-radial relationship between the second cannula 34 and the second end 22 of the endoscope 20 allows a needle or other surgical instrument that may be placed within the second cannula 34 and used in the area 35 described above, to intersect the second end 22 of the endoscope 20.

Having multiple through holes 14 in the guide 10 allows for flexibility in the placement of the second portal 33 so that damage to internal structures can be minimized. However, a guide 10 having only one through hole 14 may be used.

Figure 2:
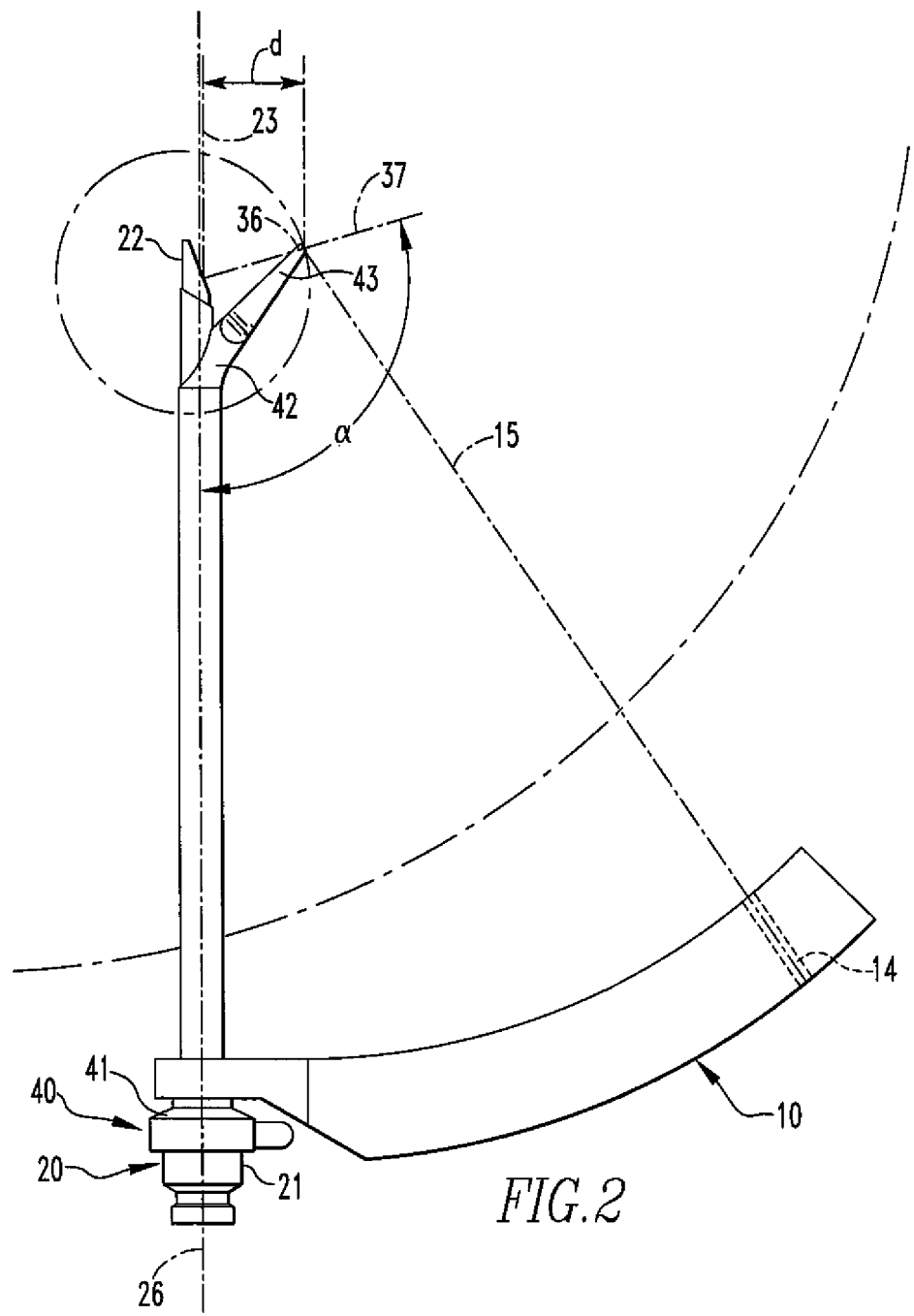

FIG. 2 shows the endoscope 20 disposed within the first cannula 40, as described above, such that the second end 22 of the endoscope 20 protrudes through a second end 42 of the cannula 40. The guide 10 is coupled to a first end 41 of the first cannula 40. The cannula 40 has a pointed tip 43, located at the second end 42, which is offset a distance d from the endoscope 20 or in a direction of view 37 of the endoscope 20. As shown in FIG. 2 and in subsequent figures, as described below, the distance d is measured from the optical center 23 of the endoscope 20. The direction of view 37 of the endoscope 20 is located at an angle $\alpha$, about 70°, relative to a longitudinal axis 26 of the endoscope 20. Sometimes, the anatomy of the body prevents the second end 22 of the endoscope 20 from being positioned in the area 36, such as the inner surface of the hip capsule as described above, where the surgeon wishes the second portal (FIG. 4, 33) to be placed. When this happens, the cannula 40 with the pointed tip 43 can be used to identify this area 36 and a longitudinal axis 15 of the guide through hole 14 could be made to intersect, or be co-radial with, the pointed tip 43. Rather than using a cannula with a pointed tip, the endoscope 20 could be fitted with a pointed tip similar to the pointed tip 43 of the cannula 40. The endoscope 20 and pointed tip could be introduced into the patient's body via a slotted cannula.

Figure 3:
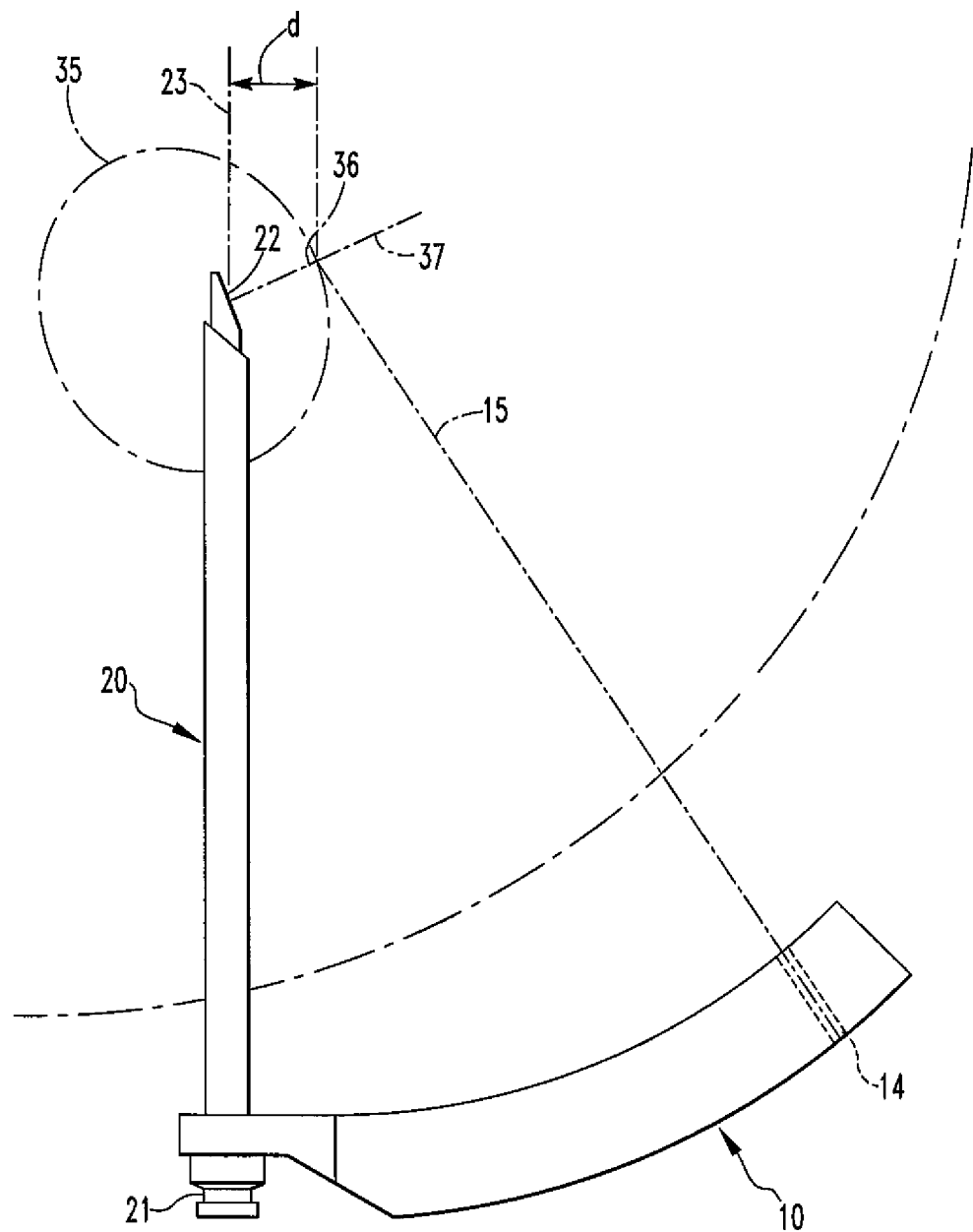

FIG. 3 is similar to FIG. 2 in that a longitudinal axis 15 of the through hole 14 intersects with an area 36 that is offset a distance d from the endoscope 20 or in a direction of view 37 of the endoscope 20. However, rather than using the pointed tip 43 of the cannula 40 to identify this area 36, the average distance d between the endoscope 20 and the point of intersection with area 36 is determined and an offset, equal to that average distance d, is built into the guide 10 so that a longitudinal axis 15 of the through hole 14 intersects with this area 36. For example, during hip arthroscopy, a surgeon may want to introduce a needle into the hip capsule 35, but the hip anatomy may prevent the second end 22 of the endoscope 20 from being brought up against the inner surface 36 of the hip capsule. Since the endoscope 20 may be a distance from the capsule inner surface 36, an error where the needle penetrates the capsule would result. To overcome this problem, the pointed tip 43 or the built-in offset d, as described above, could be used. For the purposes of this disclosure, the distance d is about 1 cm. However, the distance d will vary based on the location of the endoscope 20 relative to area 36.

Figure 4:
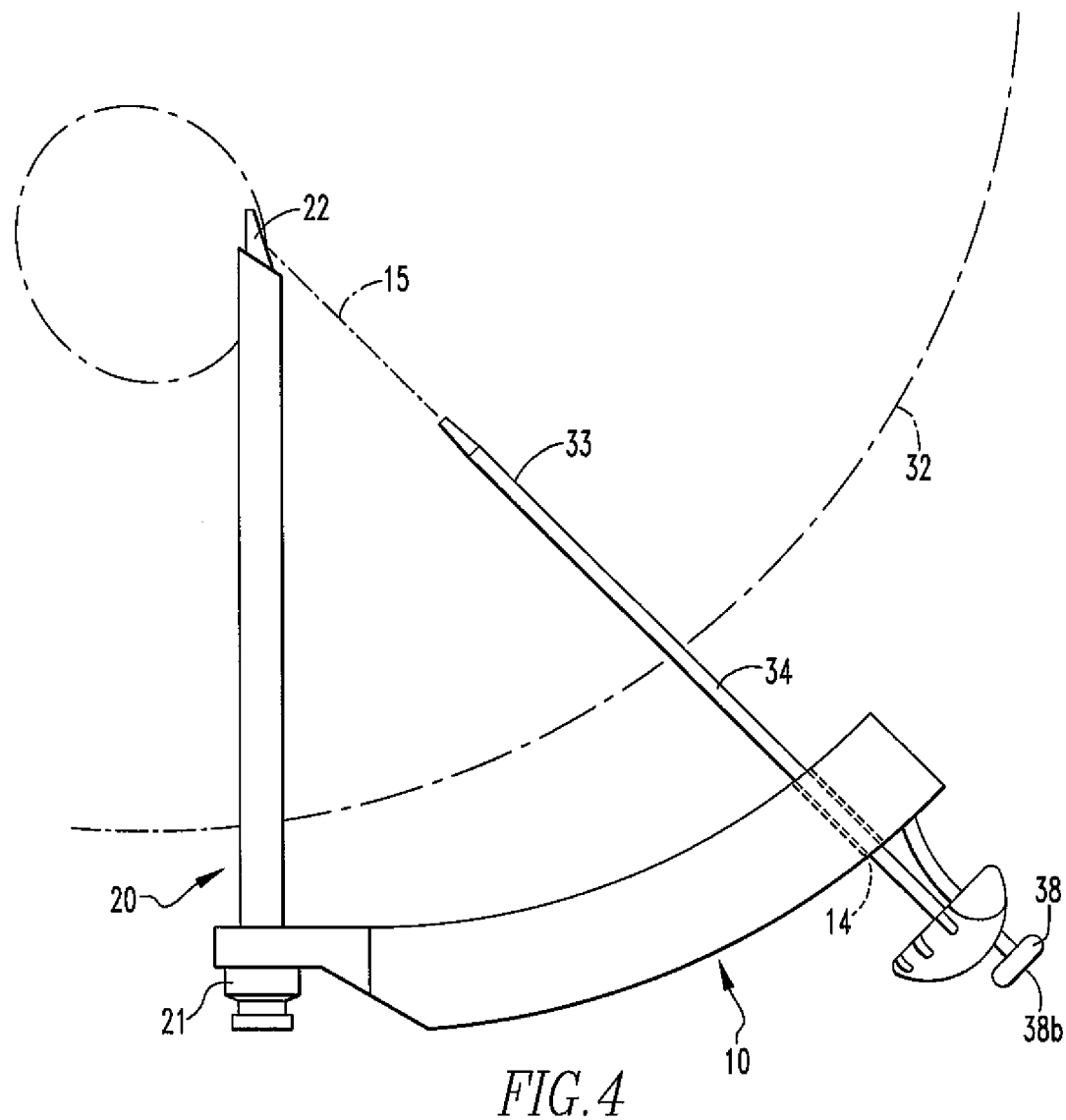

FIG. 4 shows the second cannula 34 disposed within the through hole 14 and second portal 33. The cannula 34 includes a depth stop 38 that substantially reduces the possibility of a first end 39a of a needle 39 or other surgical instrument, disposed within the cannula 34, from advancing past the second end 22 of the endoscope 20 by having a second end 39b of the needle 39 abut a second end 38b of the depth stop 38. The depth stop 38 may be part of the second cannula 34 or separate from the second cannula 34. This allows the second cannula 34 to be positioned to any depth within the through hole 14, yet still have a fixed depth stop relative to the guide 10.

Figure 5:
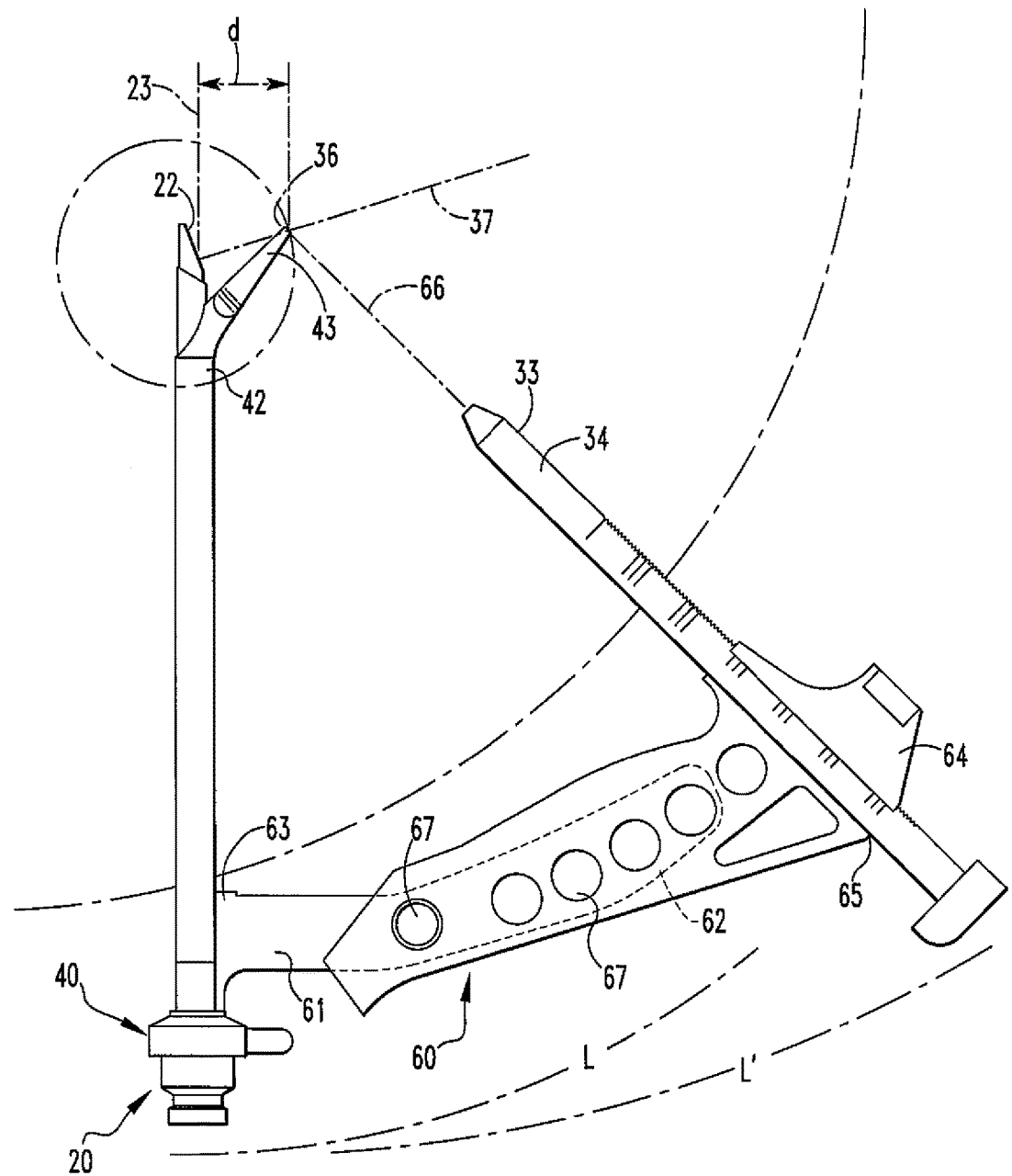
FIG. 5 shows a front view of a second guide assembly of the present disclosure.

FIG. 5 shows a guide 60 that includes a body 61 having a first end 62, a second end 63, and an arc along a length L of the body 61. The guide 60 also includes a joint 64 configured for sliding along the length L of the body 61. The joint 64 includes at least one through hole 65. Similar to the guide 10 disclosed in FIGS. 1-4, guide 60 is also coupled to a first surgical device 20, such as an endoscope. The endoscope 20 may be disposed within a first cannula 40, similar to the first cannula disclosed in FIG. 2 and described above, such that the second end 22 of the endoscope 20 protrudes through a second end 42 of the cannula 40. The cannula 40 has a pointed tip 43 similar to the pointed tip shown in FIG. 2 and described above. A second surgical device 34, similar to the second surgical device shown in FIG. 4, is disposed within the through hole 65. A longitudinal axis 66 of the through hole 65, and therefore of the second surgical device 34, intersects, or is co-radial with, the pointed tip 43. However, the longitudinal axis 66 could be made to intersect, or be co-radial with, the second end 22 of the endoscope 20 or with an area 36 that is offset a distance d from the endoscope 20, as shown in FIGS. 1 and 3.

The joint 64 may be slid along the length L of the body 61 to decide where to place the second portal 33 so that damage to internal structures can be minimized. Since the longitudinal axis 66 of the through hole 65 and the second surgical device 34 is co-radial with the pointed tip 43, a needle or other surgical instrument disposed within the second surgical device 34, will intersect the pointed tip 43, regardless of where the second portal 33 is placed. The joint 64 and the body 61 may include openings 67 to make the guide 60 lightweight and ensure that the joint 64 and body 61 cool quickly after autoclaving.

Figure 6:
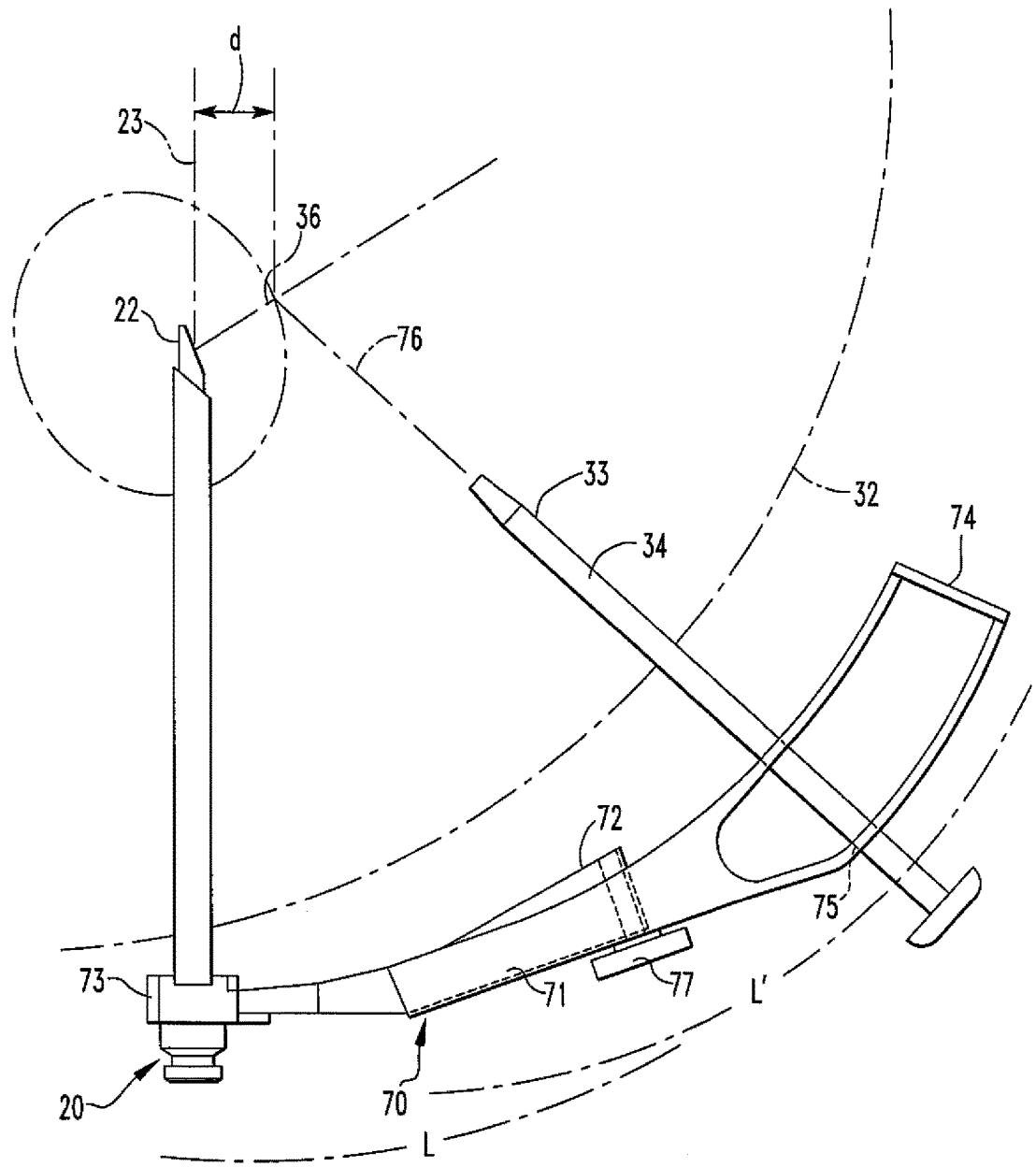
FIG. 6 shows a front view of a third guide assembly of the present disclosure.

Similar to the guide 60 shown in FIG. 5, FIG. 6 shows a guide 70 that includes a body 71 having a first end 72, and a second end 73. The guide 70 also includes a joint 74 configured for sliding along the body 71. The joint 74 includes at least one through hole 75. Similar to the guide 10 disclosed in FIGS. 1-4, guide 70 is also coupled to a first surgical device 20, such as an endoscope, via a cannula 40. A second surgical device 34, similar to the second surgical device shown in FIG. 4, is disposed within the through hole 75. A longitudinal axis 76 of the through hole 75, and therefore of the second surgical device 34, intersects, or is co-radial with, an area 36 that is offset a distance d from the endoscope 20. However, the longitudinal axis 76 could be made to intersect, or be co-radial with, a pointed tip 43 of the cannula 40 or the second end 22 of the endoscope 20, as shown in FIGS. 2, 5, 1 and 4.

As also shown in FIG. 5 and described above, the joint 74 may be slid along the body 71 to vary the distance d based upon the distance between the second end 22 of the endoscope 20 and the capsule inner surface 36. Since the second surgical device 34 is co-radial with the area 36, a needle or other surgical instrument disposed within the second surgical device 34, will intersect the area 36, regardless of where the second portal 33 is placed. The guide 70 also includes a mechanism 77, such as a locking nut, for engaging the joint 74 and holding it in a position along the body 71. Once the surgeon has determined the position of the second portal 33, the locking nut 77 will be tightened to engage the joint 74 and hold it in a position along the body 71. The second surgical device 34 will then be inserted into the through hole 75 and through the patient's body 32 to make the second portal 33.

Figure 7:
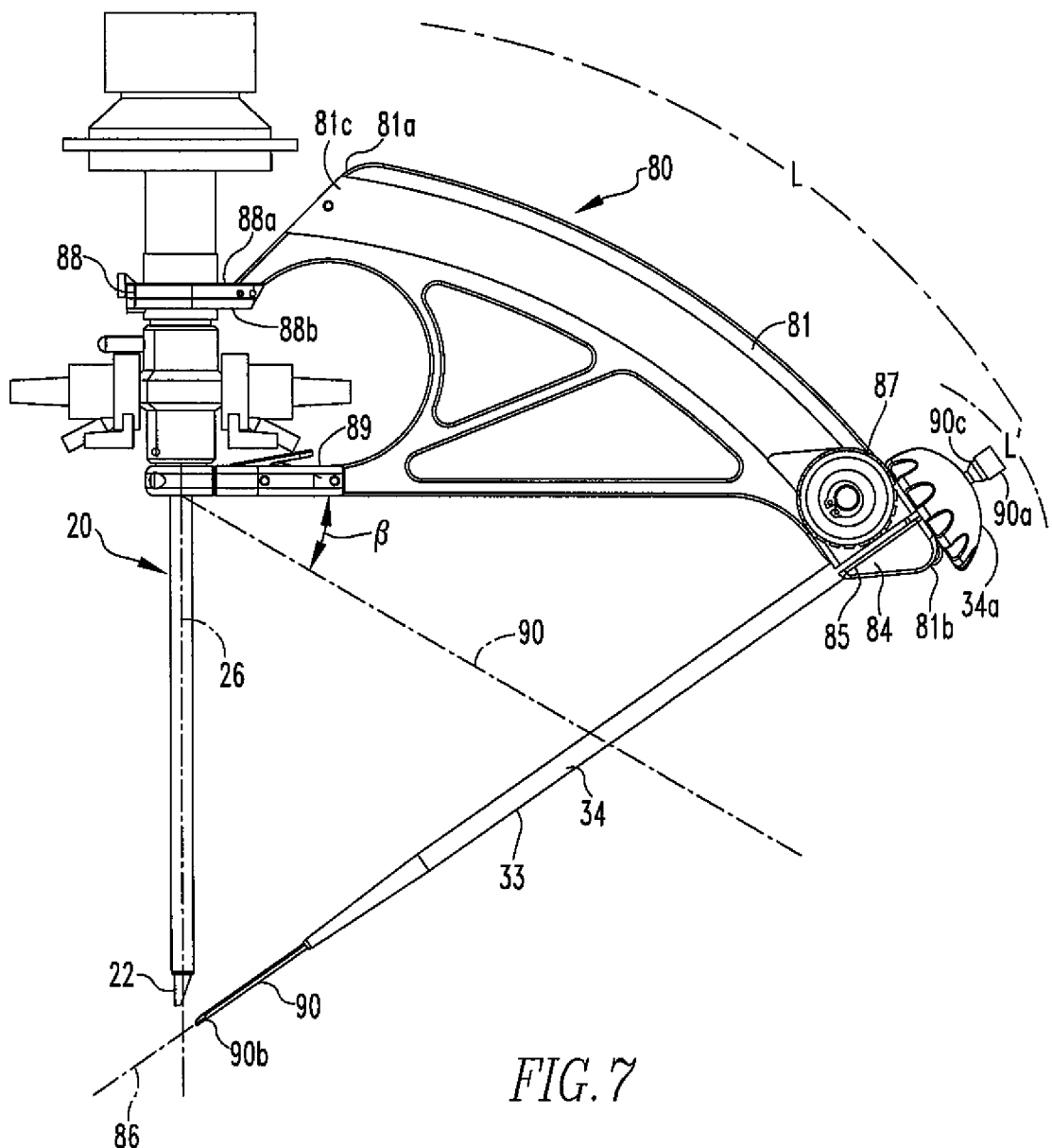
FIG. 7 shows a front view of a fourth guide assembly of the present disclosure.

Similar to the guides 60,70 shown in FIGS. 5 and 6, the guide 80 shown in FIG. 7 includes a body 81 having a first end 81a, a second end 81b, and an arc along a length L of the body 81. The guide 80 also includes a joint 84 configured for sliding along a length L of the body 81. The joint 84 includes at least one through hole 85. Similar to the guide 10, 60, 70 disclosed in FIGS. 1-6, guide 80 is also coupled to a first surgical device 20, such as an endoscope via the first end 21 of the endoscope 20 and the first end 41 of the cannula 40. A second surgical device 34, similar to the second surgical device shown in FIGS. 4-6, is disposed within the through hole 85. A longitudinal axis 86 of the through hole 85, and therefore of the second surgical device 34, intersects, or is co-radial with, the second end 22 of the endoscope 20. However, the longitudinal axis 86 could be made to intersect, or be co-radial with, a pointed tip 43 of the cannula 40 or an area 36 that is offset a distance d from the endoscope 20, as shown in FIGS. 4, 5, and 3.

As also shown in FIG. 7 and described above, the joint 84 may be slid along the length L of the body 81 to decide where to place a second portal so that damage to internal structures can be minimized. Since the second surgical device 34 is co-radial with the second end 22 of the endoscope 20, a needle 90 or other surgical instrument disposed within the second surgical device 34, will intersect the second end 22, regardless of where the second portal is placed. The body 80 includes a slot 81c that runs the entire length L of the body 80 and that houses the joint 84. In addition, similar to the guide 70 of FIG. 6, the guide 80 includes a mechanism 87, such as a locking nut, for engaging the joint 84 and holding it in a position along the body 81. During surgery, use of the locking nut 87 in creating a second portal occurs in the same manner as described above. After the second surgical device 34, or second cannula, has been inserted into the patient's body, the needle 90, or other instrument, may be inserted through the cannula 34 for use in performing a surgical procedure. The needle 90 which intersects, or is co-radial with, the second end 22 of the endoscope 20, may include a depth stop 90c, at a first end 90a of the needle 90, that abuts a first end 34a of the cannula 34 to substantially reduce the possibility of the second end 90b of the needle 90 from advancing past the second end 22 of the endoscope 20.

Figure 8:
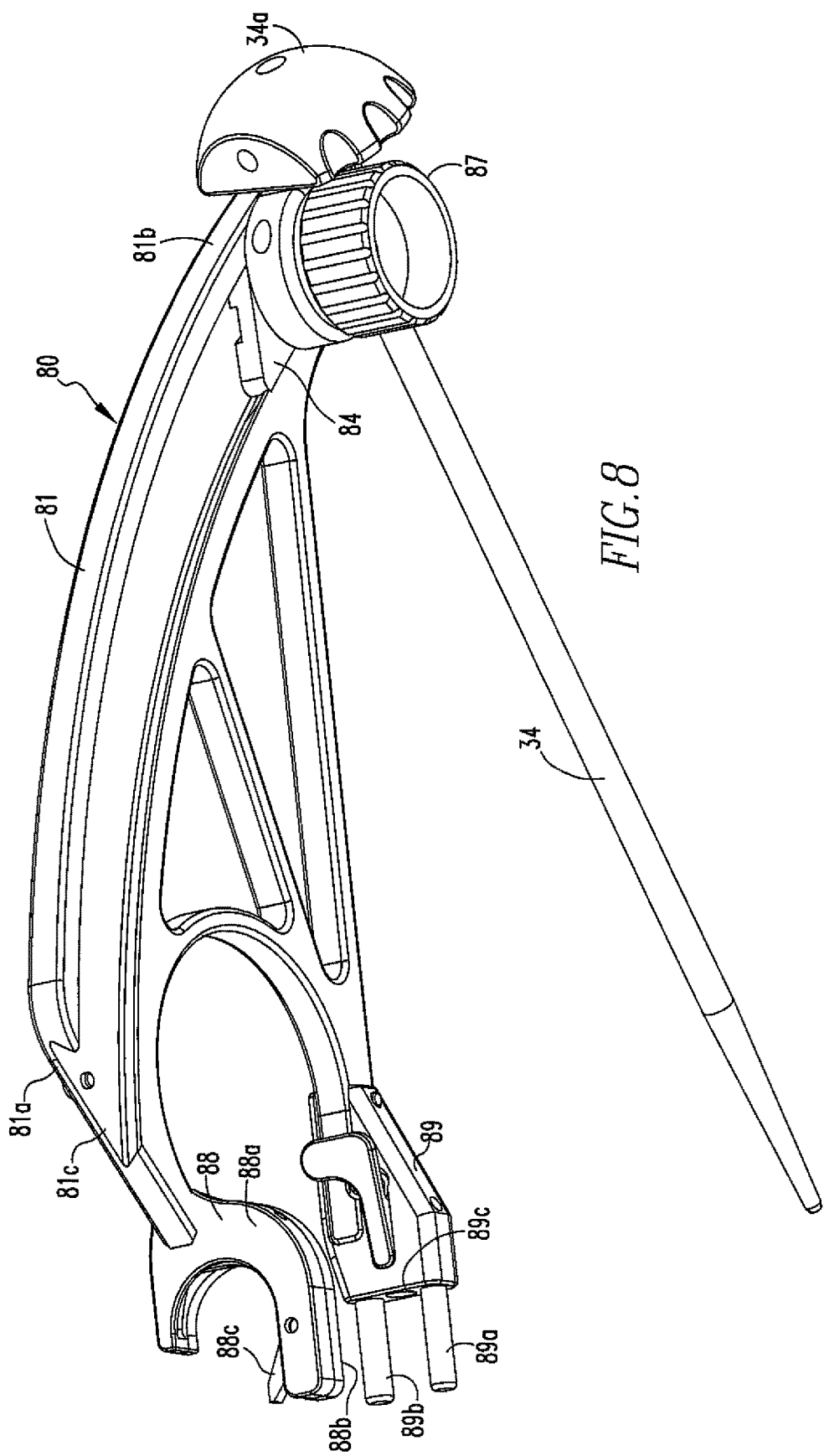
FIG. 8 shows an isometric view of the fourth guide assembly of the present disclosure.
Figure 9B:
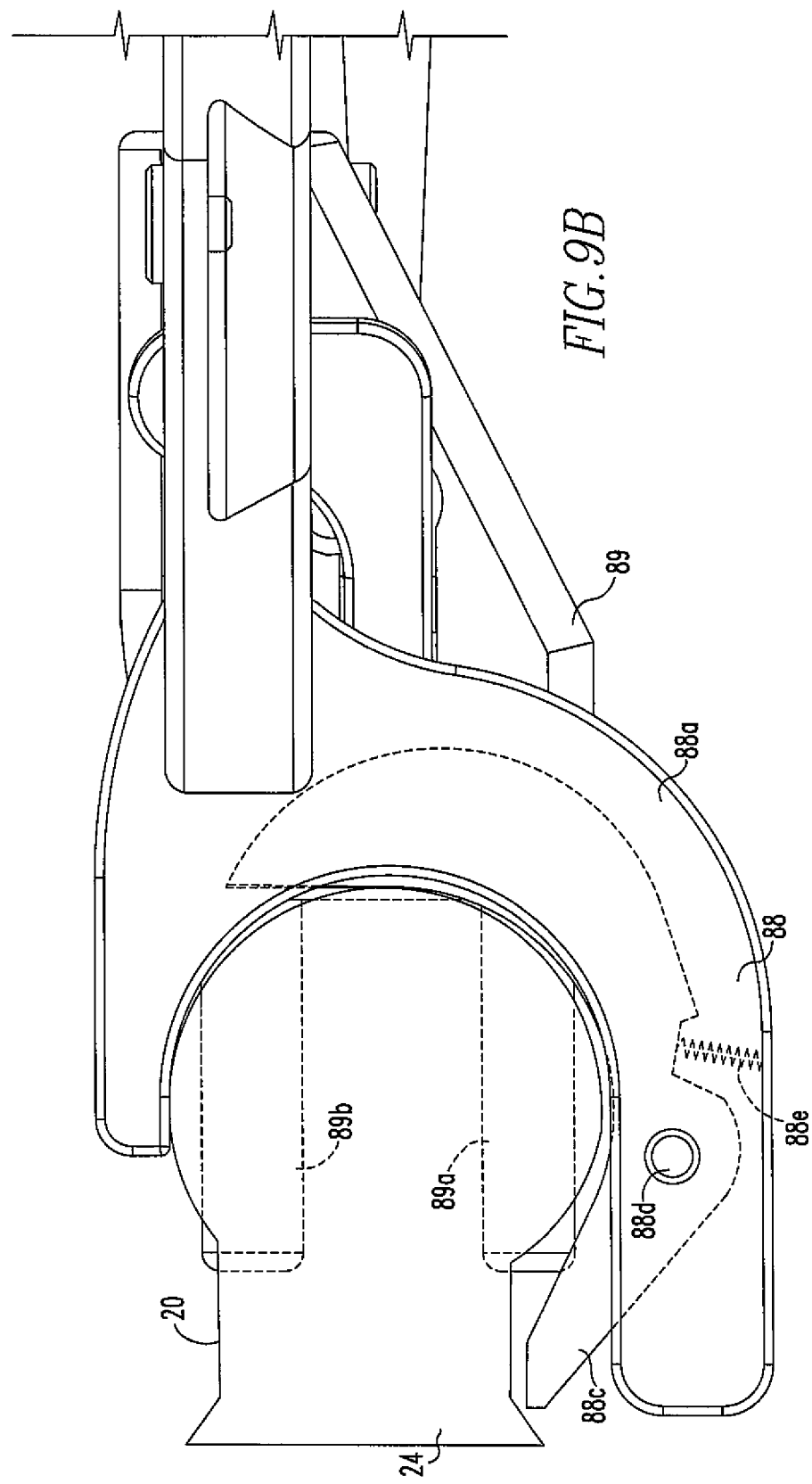
FIG. 9B shows a top view of the lever arm, of the fourth guide assembly, in a second position.

As shown in FIGS. 7 and 8, the guide 80 includes a first attachment portion 88 and a second attachment portion 89, both of which are configured for coupling the body 81 to the first surgical device 20 via the first surgical device 20 and the cannula 40. The first attachment portion 88, which includes an anti-rotation lock, is located at the first end 81a of the body 81 and extends substantially perpendicular to the axis 26 of the endoscope 20. As shown in FIGS. 9A and 9B, the anti-rotation lock 88 includes a lever arm 88c located between a top surface 88a and bottom surface 88b of the anti-rotation lock 88. The lever arm 88c is coupled to the surfaces 88a,b via a pivot pin or screw 88d and a spring 88e. When the endoscope 20 is not coupled to the anti-rotation lock 88, the lever arm 88c is in a first position, as shown in FIG. 9A, such that the spring 88e is in a relaxed state. However, when the endoscope 20 is coupled to the anti-rotation lock 88, the lever arm 88c is in a second position, as shown in FIG. 9B, such that the lever arm 88c is pushed against the light post 24 of the endoscope 20, and substantially reduces the possibility of rotation of the light post 24 in a direction that would uncouple the cannula 40 from the endoscope 20.

Figure 10:
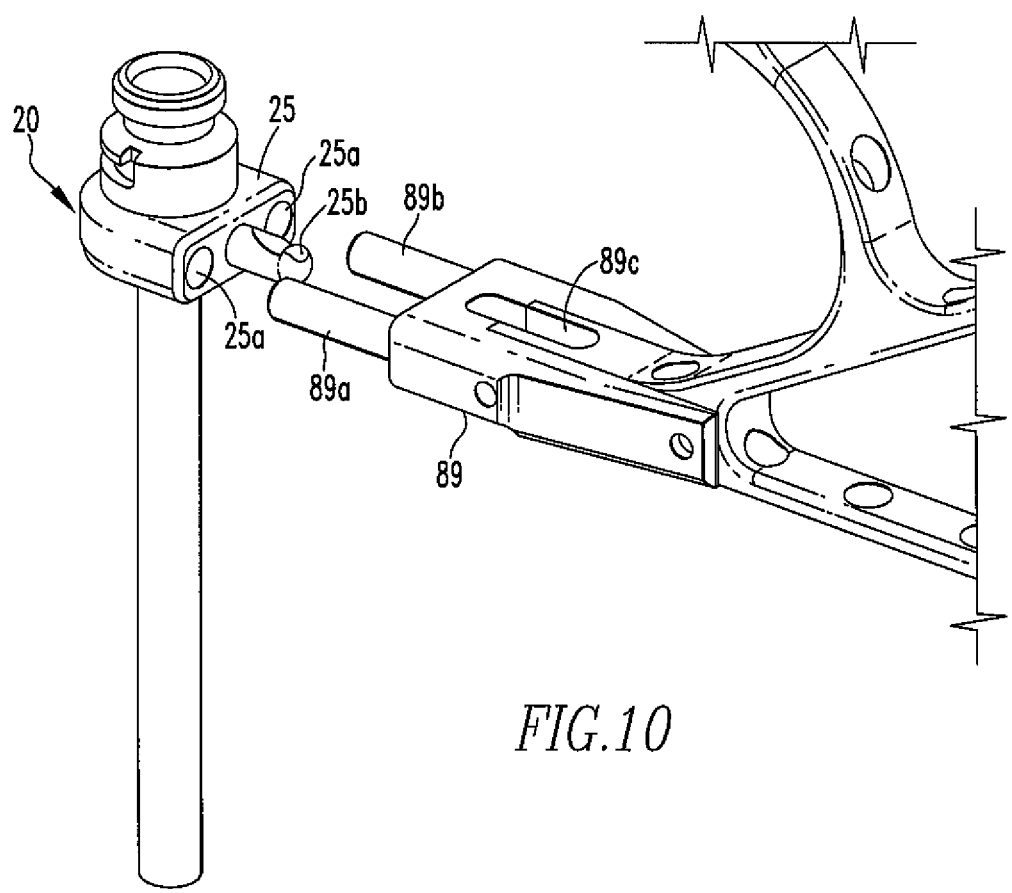
FIG. 10 shows a perspective view of the second attachment portion of the fourth guide assembly.

As shown in FIGS. 7 and 8, the second attachment portion 89 is located near the second end 81b of the body 81 and extends substantially perpendicular to the longitudinal axis 26 of the endoscope 20. The portion 89 includes two prongs 89a,b, both of which extend longitudinally from the portion 89, and an opening 89c, located between the prongs 89a,b that extends longitudinally into the portion 89. As shown in FIG. 10, the cannula 40 includes a coupling portion 45 configured for coupling of the second attachment portion 89 to the cannula 40. The coupling portion 45 includes two holes 45a and a projection 45b that extends longitudinally from the coupling portion 45. The second attachment portion 89 is coupled to the coupling portion 45 such that the prongs 89a,b are disposed within the holes 45a and the projection 45b is disposed within the opening 89c.

As shown in FIG. 7, the second end 81b of the body 81 does not extend beyond a plane 90, located between the second attachment portion 89 and a longitudinal axis 26 of the first surgical device 20, and that forms an angle β, about 60°, with the longitudinal axis 26.

Figure 11A:
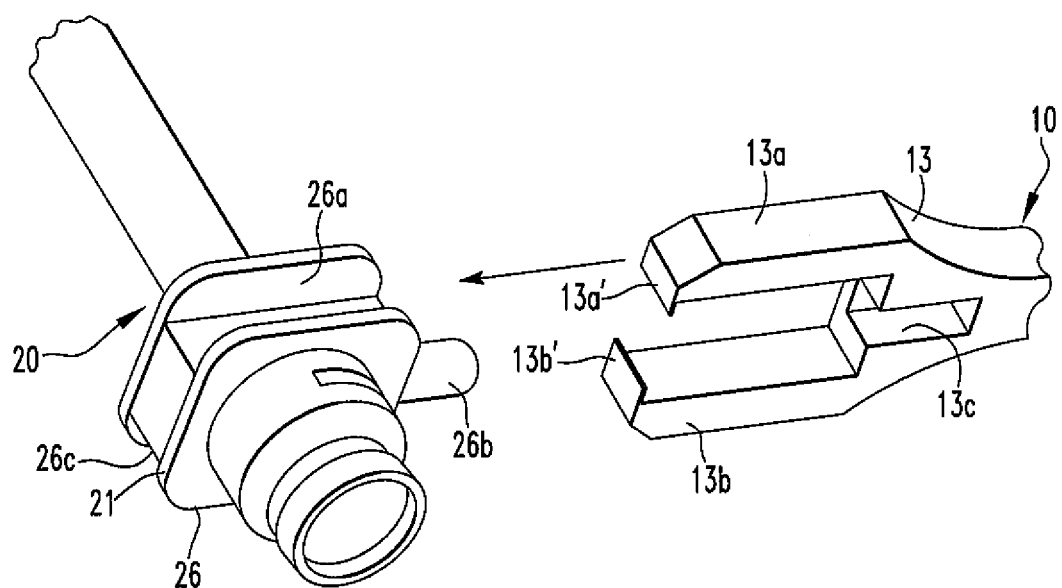
FIGS. 11A-11D show perspective views of methods for attaching the guides of the present disclosure to an endoscope cannula.
Figure 11B:
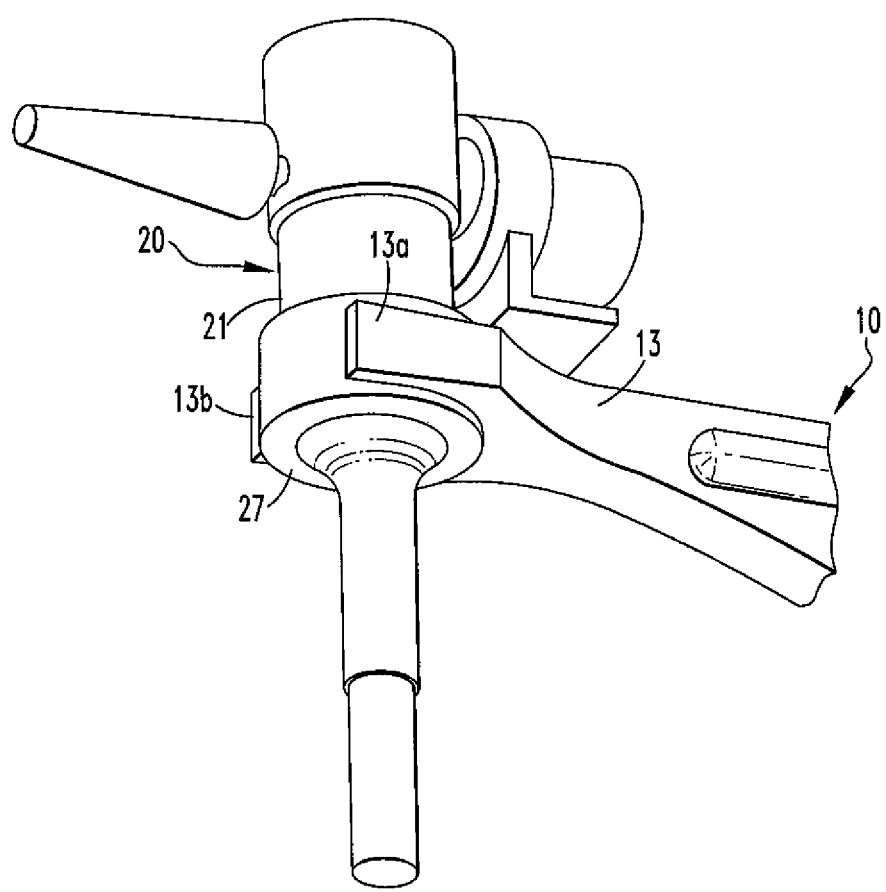
Figure 11C:
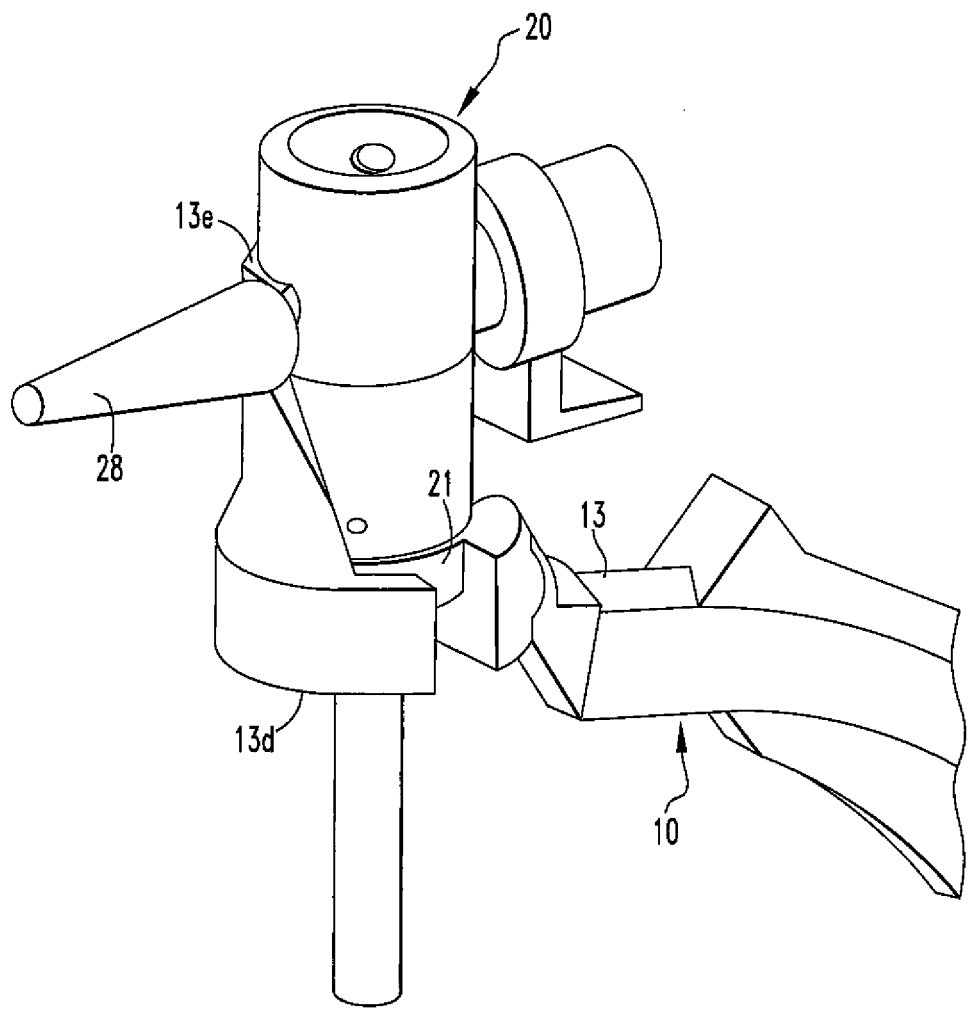

FIGS. 11A-11D show methods for coupling the second end 13 of the guide 10 to the first end 41 of the cannula 40. As shown in FIG. 11A, the second end 13 includes a first arm 13a, a second arm 13b, and a slot 13c located between the first and second arms 13a,b. The first end 41 of the cannula 40 includes a coupling portion 46, similar to the coupling portion 45 shown in FIG. 10 albeit with channels 46a instead of holes 45a. The second end 13 of the guide 10 is coupled to the first end 41 of the cannula 40 such that the first and second arms 13a,b are housed within the channels 46a and the projection 46b is housed within the slot 13c. Both arms 13a,b include an edge 13a', 13b', wherein each edge 13a', 13b' is configured for attaching to the backside 46c of the coupling portion 46 when the guide 10 is coupled to the coupling portion 46, therefore creating a snap-fit connection between the arms 13a,b and the coupling portion 46.

As shown in 11B, the second end 13 of the guide 10 includes a first arm 13a and a second arm 13b. The first end 41 of the cannula 40 includes an adaptor 47 that has been slid over the cannula 40. The first and second arms 13a,b of the guide 10 are coupled to the adaptor 47 such that an interference fit, or a clip-on connection, is created between the arms 13a,b and the adaptor 47.

Figure 11D:
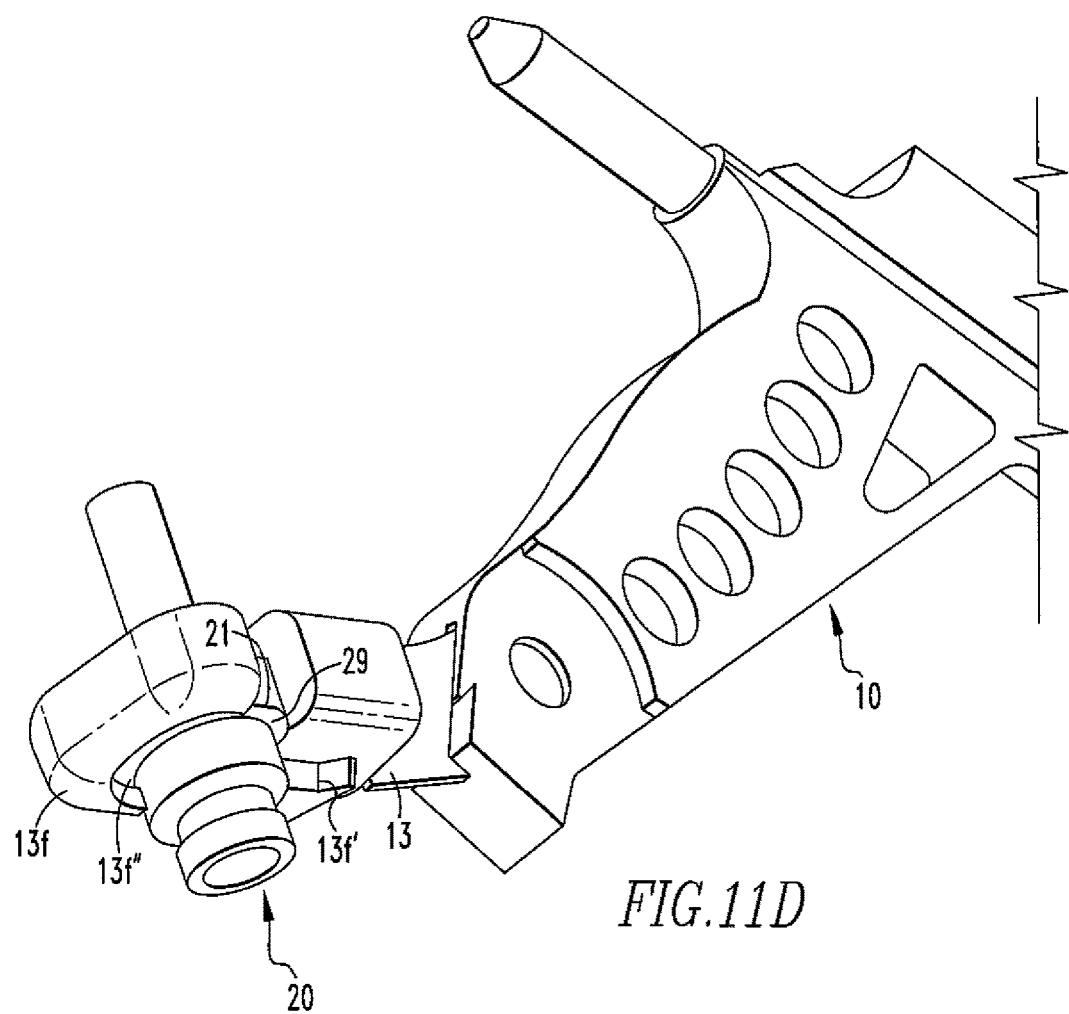

As shown in 11C, the second end 13 of the guide 10 includes a base portion 13d that partially surrounds the first end 41 of the cannula 40 and includes a hook 13e that is placed on the irrigation extender 50, which is coupled to the cannula 40. Shown in FIG. 11D is a guide 10 that includes a second end 13 having an arm 13f including an opening 13f" and a slot 13f' formed in the arm 13f. The first end 41 of the cannula 40 includes a coupling portion 49, similar to the coupling portions 45, 46 shown in FIGS. 10 and 11A, albeit without holes or channels. The second end 13 of the guide 10 is coupled to the first end 41 of the cannula 40 such that the first end 41 of the cannula 40 is disposed within the opening 13*f*" and the projection (not shown) is housed within the slot 13*f*'. The guide 10 may be placed onto the first end 41 by placing the opening 13" over the first end 41 and sliding the arm 13*f* around the coupling portion 49, so as to create a snap-fit connection between the arm 131 and the first end 41. Other methods of coupling the guide to the cannula may also be used.

Figure 12:
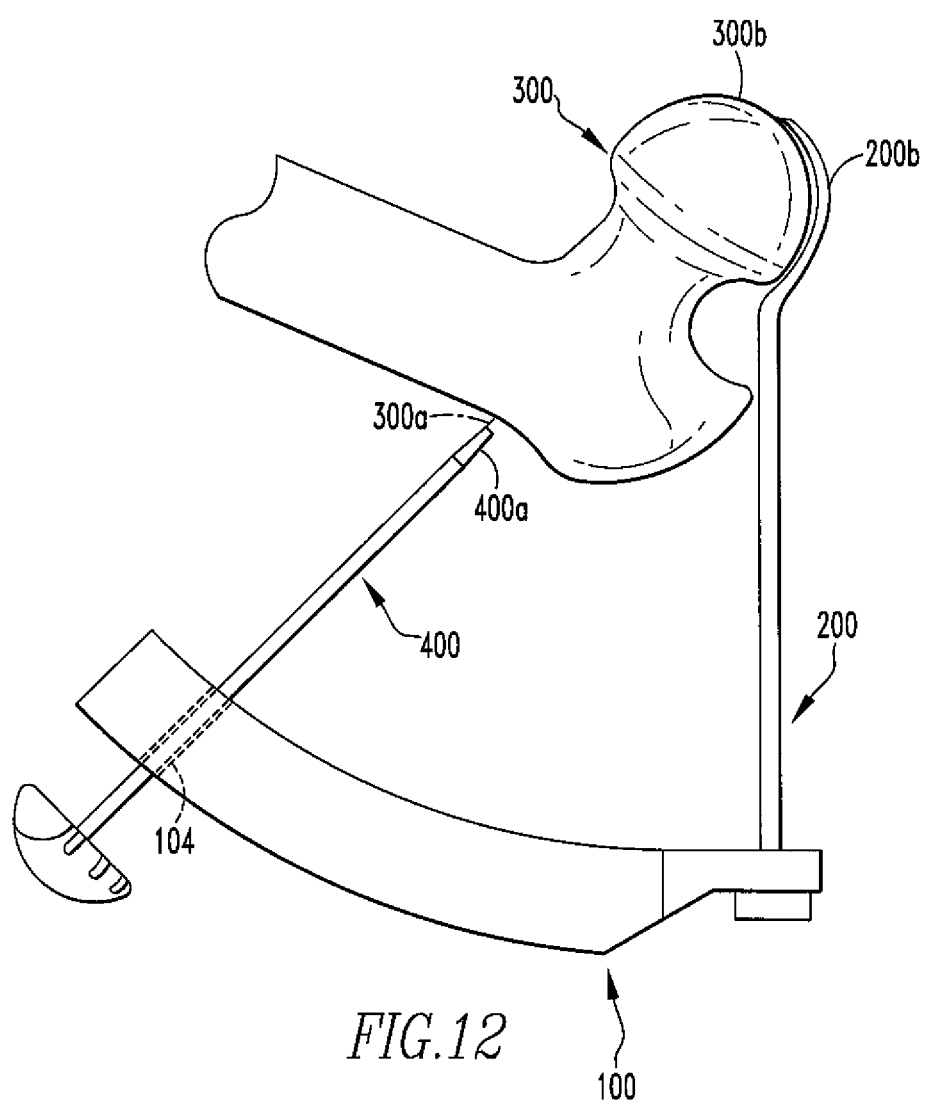
FIG. 12 shows a front view of the first guide of the present disclosure coupled to an aimer arm.

As shown in FIG. 12, a guide 100, similar to the guide 10 in FIGS. 1-4, is coupled to a first surgical device 200, such as an aimer arm, that includes a distal end 200*b* in the shape of a hook. The distal end 200*b* of the aimer arm 200 is positioned in the posterior region 300*b* of the hip joint 300. A second surgical device 400, such as a cannula, is disposed within the through hole 104 of the guide 100. A longitudinal axis 401 of the cannula 400 is co-radial with the tip 200*c* on the distal end 200*b* of the aimer arm 200. This co-radial relationship allows access to the posterior region 300*b* of the hip joint 300, via the femoral neck 300*a*, by a surgical tool, such as a drill (not shown), disposed within the cannula 400. The aimer arm 200 may be introduced into the body 32 in the same manner as the endoscope 20 is introduced, as described above, or another manner known to one of ordinary skill in the art. Likewise, the guide 100 may be coupled to the aimer arm 200 in the same manner as guide 80 is coupled to the cannula 40 in FIG. 7, in the same manner as guide 10 is coupled to the cannula 40 in FIGS. 11A-11D, or another manner known to one of ordinary skill in the art. The aimer arm 200 may rotate around a longitudinal axis 201 of the aimer arm 200 via a rotational coupling (not shown) located at the proximal end 200*a* of the aimer arm 200.

Figure 13:
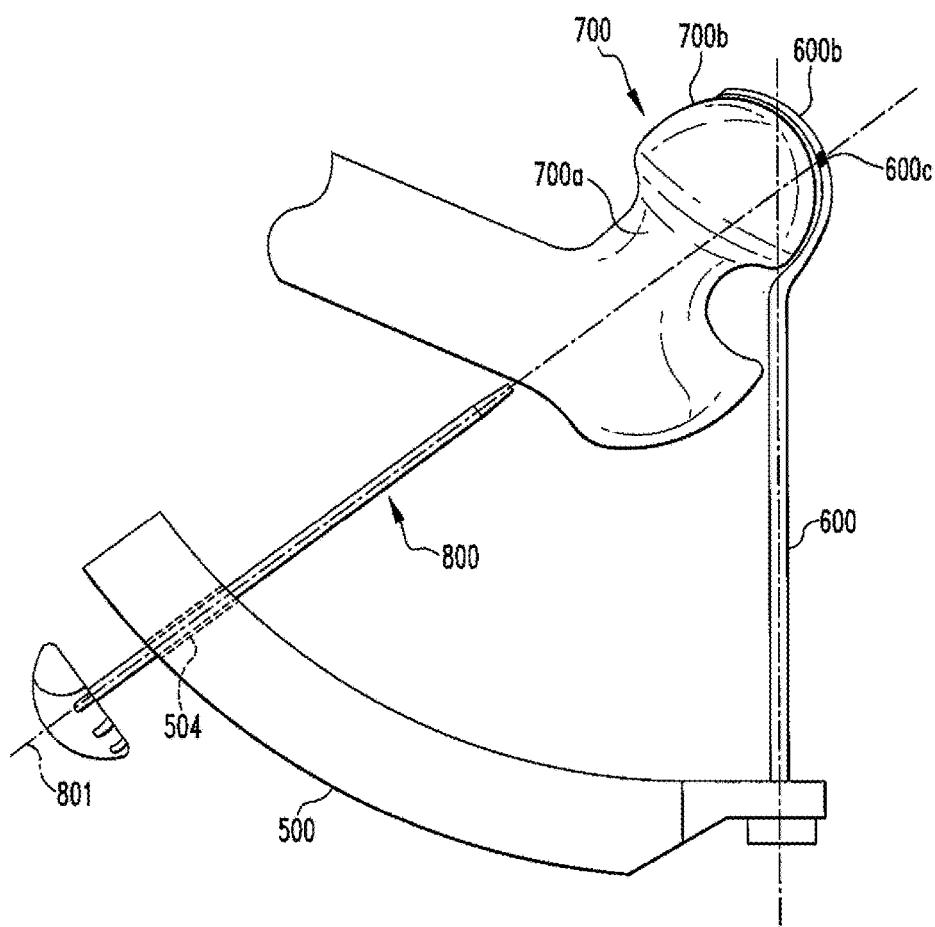
FIG. 13 shows a front view of the first guide of the present disclosure coupled to another aimer arm.

As shown in FIG. 13, a guide 500, similar to the guide 100 in FIG. 12, is coupled to a first surgical device 600, such as an aimer arm, that includes a distal end 600*b* in the shape of a hook. The distal end 600*b* of the aimer arm 600 is positioned in the posterior region 700*b* of the hip joint 700. A second surgical device 800, such as a cannula, is disposed within the through hole 504 of the guide 500. A longitudinal axis 801 of the cannula 800 is co-radial with the mark 600*c* on the distal end 600*b* of the aimer arm 600. This co-radial relationship allows access to the posterior region 700*b* of the hip joint 700, via the femoral neck 700*a*, by a surgical tool, such as a drill (not shown), disposed within the cannula 800. The aimer arm 600 may be introduced into the body in the same manner as the endoscope 20 is introduced, as described above, or another manner known to one of ordinary skill in the art. Likewise, the guide 500 may be coupled to the aimer arm 600 in the same manner as guide 10 is coupled to the cannula 40 in FIGS. 11A-11D, or another manner known to one of ordinary skill in the art. Furthermore, the mark 600*c*, which may be created by a laser or any other technology that could be used to create the mark, may be located anywhere along the hook 600*b*. Mark 600*c* may also be a physical feature, such as a bump, a hole, or any other physical feature that may be seen on an X-ray.

Figure 14:
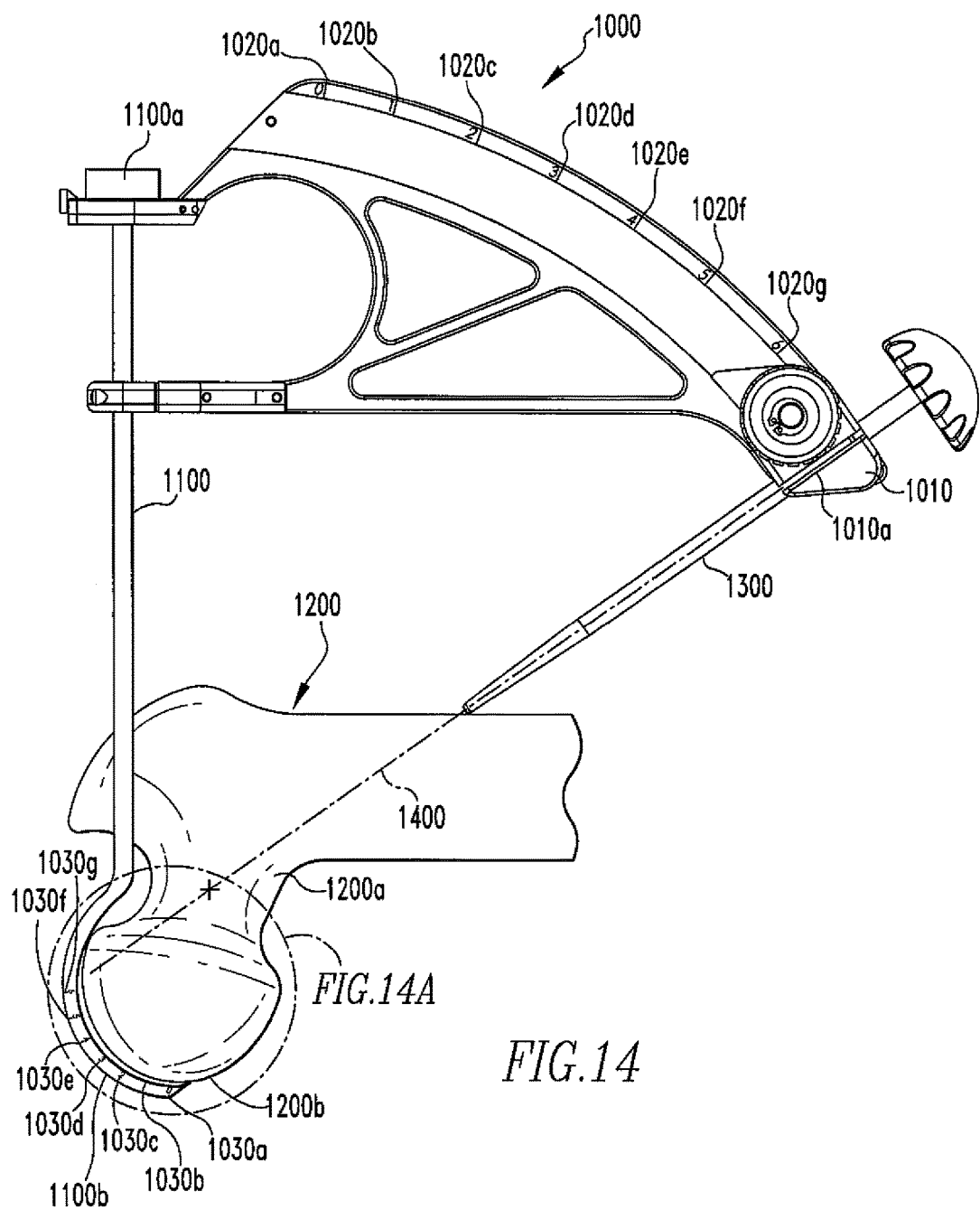
FIG. 14 shows a front view of the fourth guide of the present disclosure coupled to an aimer arm.
Figure 14A:
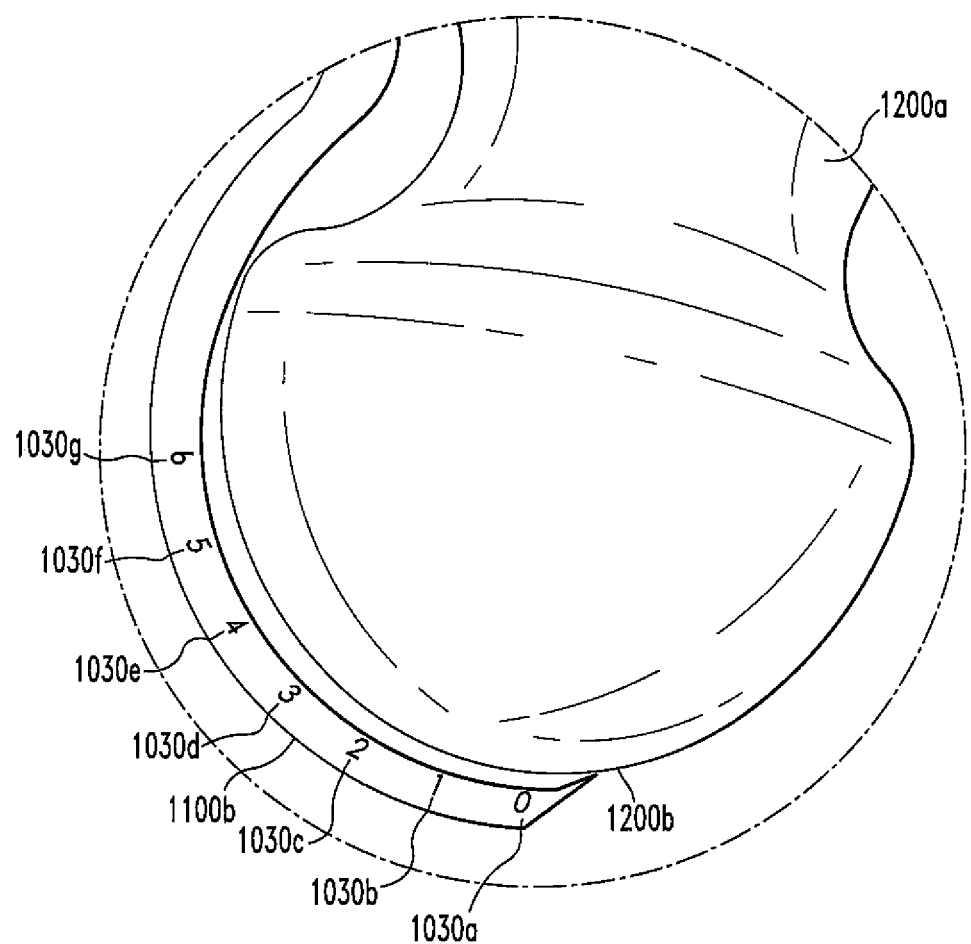
FIG. 14A shows an expanded view of a distal end of the aimer arm of the guide of FIG. 14.

As shown in FIGS. 14 and 14A, a guide 1000, similar to the guide 80 in FIG. 7, is coupled to a first surgical device 1100, such as an aimer arm, that includes a distal end 1100*b* in the shape of a hook. The distal end 1100*b* of the aimer arm 1100 is positioned in the posterior region 1200*b* of the hip joint 1200. A second surgical device 1300, such as a cannula, is disposed within the through hole 1010*a* of the joint 1010. The guide 1000 includes a first set of marks 1020*a*-1020*g* and the distal end 1100*b* of device 1100 includes a second set of marks 1030*a*-1030*g*, as more clearly shown in FIG. 14A. A mark of the first set of marks 1020*a*-1020*g* and a mark of the second set of marks 1030*a*-1030*g* are co-radial. For example, as shown in FIG. 14, the longitudinal axis 1400 of device 1300 is co-radial with mark 1030*g* when joint 1010 is located at mark 1020*g*. This co-radial relationship allows access to the posterior region 1200*b* of the hip joint 1200, via the femoral neck 1200*a*, by a surgical tool, such as a drill (not shown), disposed within the cannula 1300. During use, the joint 1010 is moved to a mark or marker of the first set of marks 1020*a*-1020*g* and the drill (not shown) is then inserted into the cannula 1300.

The aimer arm 1100 may be introduced into the body in the same manner as the endoscope 20 is introduced, as described above, or another manner known to one of ordinary skill in the art. Likewise, the guide 1000 may be coupled to the aimer arm 1100 in the same manner as guide 10 is coupled to the cannula 40 in FIGS. 11A-11D, or another manner known to one of ordinary skill in the art. Furthermore, the marks 1020, 1030 may be created by a laser or any other technology that could be used to create the marks.

For the purposes of this disclosure, a manual or automatic milling machine is used to create the through holes of the guides described above. Other apparatuses and methods of creating the through holes may also be used. The guides are manufactured from a metal material, such as stainless steel or titanium, but may be manufactured from another material known to one of ordinary skill in the art. In addition, the first and second cannulas and the aimer arm described above are manufactured from a biocompatible metal material, such as stainless steel, but may be manufactured from another biocompatible material known to one of ordinary skill in the art. Furthermore, for the purposes of this disclosure, the guides include a body having an arc along the length of the body, but an arc is not necessary and the body may be straight or incorporate any other shapes known to one of ordinary skill in the art. Although the present disclosure relates to the use of the above described guides for the placement of portals during hip arthroscopy, the basic principles and methods may also be applied to other joint areas of the body.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting.

What is claimed is:
1. A guide assembly comprising:
a guide including a body having a first set of a plurality of marks and a joint including at least one through hole, the joint configured for sliding along the length of the body; and
a first surgical device coupled with respect to the guide, the first surgical device defining a longitudinal axis and including an elongated body with a distal end defining a curved surface, the curved surface configured to correspond with a curvature of a femoral head so as to enable engaging the curved surface with the femoral head;
wherein a first longitudinal axis of the through hole is defined for a first position of the joint corresponding to a first of the plurality of the marks and a second longitudinal axis of the through hole is defined for a second position of the joint corresponding to a second of the plurality of the marks;

wherein the first longitudinal axis and the second longitudinal axis intersect a point in between the guide and the first surgical device; and wherein the first longitudinal axis of the through hole and the second longitudinal axis of the through hole are configured to guide access of a second surgical device to a region of the hip joint via different paths through the femoral neck when the first surgical device is engaged with the femoral head and the second surgical device is received in the through hole.

2. The guide assembly of claim 1, further comprising a second surgical device disposed within the through hole.

3. The guide assembly of claim 2, wherein the second surgical device is a cannula.

4. The guide assembly of claim 3, wherein the cannula is configured to receive a drill.

5. The guide assembly of claim 1, wherein the marks are selected from the group consisting of a laser mark, a bump, and a hole.

6. The guide assembly of claim 1, wherein the guide is removably coupled to the first surgical device.

7. A guide assembly comprising:
a first surgical device defining a longitudinal axis and including an elongated body with a distal end defining a curved surface, the curved surface configured to correspond with a curvature of a femoral head so as to enable engaging the curved surface with the femoral head at a region of a hip joint; and a guide portion extending from the longitudinal axis of the first surgical device and terminating at an end, the guide portion including a joint that defines a through hole the through hole configured to receive a second surgical device therethrough;

wherein the joint is configured for sliding along a length of the body wherein a first longitudinal axis of the through hole is defined for a first position of the joint and a second longitudinal axis of the through hole is defined for a second position of the joint;

wherein the first longitudinal axis of the through hole and the second longitudinal axis of the through hole are configured to guide access of the second surgical device to a region of the hip joint via different paths through the femoral neck when the first surgical device is engaged with the femoral head and the second surgical device is received in the through hole.

8. The guide assembly of claim 7, wherein the second surgical device is disposed within the through hole.

9. The guide assembly of claim 8, wherein the second surgical device is a cannula.

10. The guide assembly of claim 9, wherein the cannula is configured to receive a drill.

11. The guide assembly of claim 7, wherein the first longitudinal axis and second longitudinal axis are configured to extend through substantially a same point of the femoral neck when the first surgical device is engaged with the femoral head.

12. The guide assembly of claim 7, wherein the first longitudinal axis and second longitudinal axis are configured to intersect different points of the femoral head when the first surgical device is engaged with the femoral head.

13. The guide assembly of claim 7, wherein the first longitudinal axis of the through hole is configured to substantially align with an axis of the femoral neck when the first surgical device is engaged with the femoral head.

14. The guide assembly of claim 7, wherein the second longitudinal axis of the through hole is configured to be at an angle relative to an axis of the femoral neck when the first surgical device is engaged with the femoral head.

* * * * *